(12) United States Patent
Knust et al.

(10) Patent No.: US 8,618,303 B2
(45) Date of Patent: *Dec. 31, 2013

(54) PYRROLIDINE DERIVATIVES

(75) Inventors: Henner Knust, Rheinfelden (DE);
 Matthias Nettekoven, Grenzach-Wyhlen (DE); Hasane Ratni, Habsheim (FR);
 Walter Vifian, Gelterkinden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/342,122

(22) Filed: Jan. 2, 2012

(65) Prior Publication Data

US 2012/0178761 A1 Jul. 12, 2012

(30) Foreign Application Priority Data

Jan. 7, 2011 (EP) ..................................... 11150352

(51) Int. Cl.
 *C07D 401/06* (2006.01)
 *A61K 31/445* (2006.01)

(52) U.S. Cl.
 USPC .......................................... 546/208; 514/324

(58) Field of Classification Search
 USPC .......................................... 546/208; 514/324
 See application file for complete search history.

(56) References Cited

U.S. PATENT DOCUMENTS

| 8,022,099 B2 * | 9/2011 | Bissantz et al. ............... 514/426 |
| 2011/0144081 A1 * | 6/2011 | Knust et al. ............... 514/210.02 |
| 2011/0152233 A1 * | 6/2011 | Knust et al. ............... 514/210.02 |

FOREIGN PATENT DOCUMENTS

| WO | 2008/128891 | 10/2008 |
| WO | 2010/040663 | 4/2010 |
| WO | 2010/094667 | 8/2010 |
| WO | 2011/073160 | 6/2011 |
| WO | 2011/085886 | 7/2011 |

OTHER PUBLICATIONS

Marco et al., "Neuropeptides" 32:481-488 ( 1998).
Jung et al., "Neuroscience" 74:403-414 ( 1996).
Giardina et al., "Exp. Opin. Ther. Patents" 10:939-960 ( 2000).
Kamali, F., "Current Opinion in Investigational Drugs" 2(7):950-956 ( 2001).
"International Search Report PCT/EP2012/050034—mailed Feb. 8, 2012."
Tooney et al., "Neurosci. Letters" 283:185-188 ( 2000).

* cited by examiner

*Primary Examiner* — Robert Havlin

(57) ABSTRACT

The invention provides compounds of formula

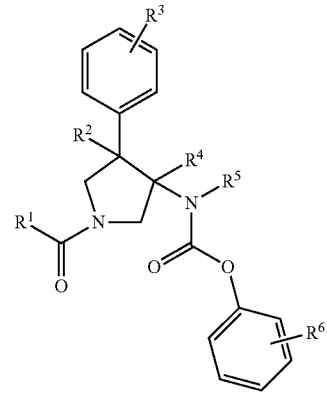

wherein $R^1$, $R^2$, $R^3$, $R^4$, $R^5$, and $R^6$ are as defined herein or a pharmaceutically suitable acid addition salt thereof. The present compounds are high potential NK-3 receptor antagonists useful for the treatment of depression, pain, psychosis, Parkinson's disease, schizophrenia, anxiety and attention deficit hyperactivity disorder (ADHD).

17 Claims, No Drawings

PYRROLIDINE DERIVATIVES

PRIORITY TO RELATED APPLICATION(S)

This application claims the benefit of European Patent Application No. 11150352.0, filed Jan. 7, 2011, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001,2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.). Objects of the present invention are novel compounds of formula I, their manufacture, medicaments based on a compound in accordance with the invention and their production as well as the use of compounds of formula I in the control or prevention of illnesses such as depression, pain, bipolar disorders, psychosis, Parkinson's disease, schizophrenia, anxiety and attention deficit hyperactivity disorder (ADHD).

SUMMARY OF THE INVENTION

The invention provides compounds of formula

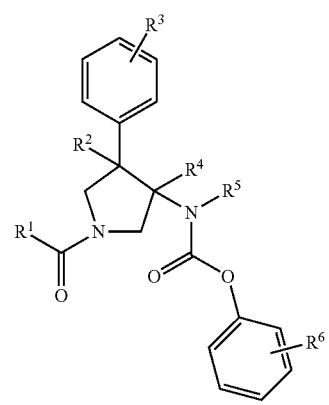

wherein
R$^1$ is

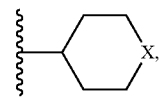

or is phenyl, pyridinyl or pyridazinyl, wherein phenyl, pyridinyl and pyridazinyl are each optionally substituted by cyano, lower alkyl, halogen-substituted phenyl, lower alkyl-substituted [1,2,4]oxadiazol-3-yl or by 2-oxo-piperidin-1-yl;

X is NR or O;

R is —C(O)-lower alkyl, —C(O)-cycloalkyl substituted by lower alkyl, cycloalkyl or is phenyl, pyridinyl or pyridazinyl, wherein phenyl, pyridinyl and pyridazinyl are each optionally substituted by lower alkyl, lower alkoxy, cyano, —C(O)-lower alkyl, halogen or lower alkyl substituted by halogen;

$R^2$ is hydrogen or lower alkyl;

$R^3$ is hydrogen, halogen, cyano, lower alkyl or lower alkyl substituted by halogen;

$R^4$ is hydrogen or lower alkyl; wherein $R^2$ and $R^4$ are not simultaneously hydrogen or lower alkyl;

$R^5$ is lower alkyl; and $R^6$ is halogen, hydroxy, lower alkyl, lower alkoxy, lower alkyl substituted by halogen, $S(O)_2$-lower alkyl or cyano;

or to a pharmaceutically suitable acid addition salt thereof.

The invention includes all racemic mixtures, all their corresponding enantiomers and/or optical isomers. In addition, all tautomeric forms of compounds of formula I are also encompassed by the present invention.

The present compounds are high potential NK-3 receptor antagonists useful for the treatment of depression, pain, psychosis, Parkinson's disease, schizophrenia, anxiety and attention deficit hyperactivity disorder (ADHD).

Preferred indications are depression, psychosis, Parkinson's disease, schizophrenia, anxiety and attention deficit hyperactivity disorder (ADHD).

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group OR, wherein R is a lower alkyl group as defined above.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

The term "halogen" denotes chlorine, iodine, fluorine and bromine.

The term "cycloalkyl" denotes an alkylene ring containing from 3 to 6 carbon ring atoms.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "pharmaceutically acceptable carrier" denotes any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

One embodiment of the invention provides compounds, wherein $R^3$ and $R^6$ are halogen.

A further embodiment of the invention provides compounds, wherein $R^4$ is methyl and $R^2$ is hydrogen, for example the following compounds rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester;

rac-[(3R,4S)-4-(4-Chloro-phenyl)-1-(1-cyclohexyl-piperidine-4-carbonyl)-3-methyl-pyrrolidin-3-yl]-methyl-carbamic acid 4-fluoro-phenyl ester;

rac-[(3R,4S)-4-(4-Chloro-phenyl)-1-(4-cyano-benzoyl)-3-methyl-pyrrolidin-3-yl]-methyl-carbamic acid 4-fluoro-phenyl ester;

rac-[(3R,4S)-1-(1-Acetyl-piperidine-4-carbonyl)-4-(4-chloro-phenyl)-3-methyl-pyrrolidin-3-yl]-methyl-carbamic acid 4-fluoro-phenyl ester;

rac-[(3R,4S)-4-(4-Chloro-phenyl)-3-methyl-1-(tetrahydro-pyran-4-carbonyl)-pyrrolidin-3-yl]-methyl-carbamic acid 4-fluoro-phenyl ester;

rac-[(3R,4S)-4-(4-Chloro-phenyl)-3-methyl-1-(6-methyl-pyridazine-4-carbonyl)-pyrrolidin-3-yl]-methyl-carbamic acid 4-fluoro-phenyl ester;

rac-{(3R,4S)-4-(4-Chloro-phenyl)-3-methyl-1 -[1 -(1-methyl-cyclopropanecarbonyl)-piperidine-4-carbonyl]-pyrrolidin-3-yl}-methyl-carbamic acid 4-fluoro-phenyl ester;

rac-[(3R,4S)-4-(4-Chloro-phenyl)-3-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3R,4S)-4-(4-Chloro-phenyl)-1-(5'-cyano-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-{(3R,4S)-4-(4-Chloro-phenyl)-1-[1-(4-cyano-phenyl)-piperidine-4-carbonyl]-3-methyl-pyrrolidin-3-yl}-methyl-carbamic acid 4-fluoro-phenyl ester;

rac-[(3R,4S)-1-(5'-Acetyl-3,4,5,6-tetrahydro-2H-[1,2']bipyridinyl-4-carbonyl)-4-(4-chloro-phenyl)-3-methyl-pyrrolidin-3-yl]-methyl-carbamic acid 4-fluoro-phenyl ester;

rac-[(3R,4S)-4-(4-Chloro-phenyl)-1-(5'-fluoro-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-[(3R,4S)-4-(4-Chloro-phenyl)-1-(5'-chloro-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-[(3R,4S)-4-(4-Chloro-phenyl)-1-(6-cyano-pyridine-3-carbonyl)-3-methyl-pyrrolidin-3-yl]-methyl-carbamic acid 4-fluoro-phenyl ester;

rac-[(3R,4S)-4-(4-Chloro-phenyl)-3-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

rac-[(3R,4S)-4-(4-Chloro-phenyl)-1-(4'-fluoro-biphenyl-4-carbonyl)-3-methyl-pyrrolidin-3-yl]-methyl-carbamic acid 4-fluoro-phenyl ester;

rac-{(3R,4S)-4-(4-Chloro-phenyl)-3-methyl-1 -[4-(5-methyl-[1,2,4]oxadiazol-3-yl)-benzoyl]-pyrrolidin-3-yl}-methyl-carbamic acid 4-fluoro-phenyl ester;

rac-[(3R,4S)-4-(4-Chloro-phenyl)-1-(6'-cyano-3,4,5,6-tetrahydro-2H-[1,3']bipyridinyl-4-carbonyl)-3-methyl-pyrrolidin-3-yl]-methyl-carbamic acid 4-fluoro-phenyl ester;

rac-{(3R,4S)-4-(4-Chloro-phenyl)-1-[1-(6-methoxy-pyridazin-3-yl)-piperidine-4-carbonyl]-3-methyl-pyrrolidin-3-yl}-methyl-carbamic acid 4-fluoro-phenyl ester; and rac-{(3R,4S)-4-(4-Chloro-phenyl)-3-methyl-1-[4-(2-oxo-piperidin-1-yl)-benzoyl]-pyrrolidin-3-yl }-methyl-carbamic acid 4-fluoro-phenyl ester;

A further embodiment of the invention provides compounds, wherein R⁴ is hydrogen and R² is methyl, for example the following compounds rac-{(3S,4R)-4-(4-Chloro-phenyl)-4-methyl-1-[1-(1-methyl-cyclopropanecarbonyl)-piperidine-4-carbonyl]-pyrrolidin-3-yl}-methyl-carbamic acid 4-fluoro-phenyl ester;

rac-{(3S,4R)-4-(4-Chloro-phenyl)-1-[1-(4-cyano-phenyl)-piperidine-4-carbonyl]-4-methyl-pyrrolidin-3-yl}-methyl-carbamic acid 4-fluoro-phenyl ester;

rac-[(3S,4R)-4-(4-Chloro-phenyl)-1-(5'-fluoro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-1-(1-isobutyryl-piperidine-4-carbonyl)-4-methyl-pyrrolidin-3-yl]-methyl-carbamic acid 4-fluoro-phenyl ester;

[(3S,4R)-4-(4-Chloro-phenyl)-1-(1-cyclohexyl-piperidine-4-carbonyl)-4-methyl-pyrrolidin-3-yl]-methyl-carbamic acid 4-fluoro-phenyl ester;

rac-[(3S,4R)-4-(4-Chloro-phenyl)-1-(4-cyano-benzoyl)-4-methyl-pyrrolidin-3-yl]-methyl-carbamic acid 4-fluoro-phenyl ester;

rac-[(3S,4R)-1-(1-Acetyl-piperidine-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-4-methyl-1-(tetrahydro-pyran-4-carbonyl)-pyrrolidin-3-yl]-methyl-carbamic acid 4-fluoro-phenyl ester;

rac-[(3S,4R)-4-(4-Chloro-phenyl)-4-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(5'-cyano-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-1-(5'-Acetyl-3,4,5,6-tetrahydro-2H-[1,2']bipyridinyl-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-1-(5'-chloro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-4-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(6'-cyano-3,4,5,6-tetrahydro-2H-[1,3']bipyridinyl-4-carbonyl)-4-methyl-pyrrolidin-3-yl]-methyl-carbamic acid 4-fluoro-phenyl ester;

rac-{(3S,4R)-4-(4-Chloro-phenyl)-1-[1-(6-methoxy-pyridazin-3-yl)-piperidine-4-carbonyl]-4-methyl-pyrrolidin-3-yl}-methyl-carbamic acid 4-fluoro-phenyl ester; and rac-{(3S,4R)-4-(4-Chloro-phenyl)-4-methyl-1-[4-(2-oxo-piperidin-1-yl)-benzoyl]-pyrrolidin-3-yl}-methyl-carbamic acid 4-fluoro-phenyl ester;

One further embodiment of the invention provides compounds of formula Ia,

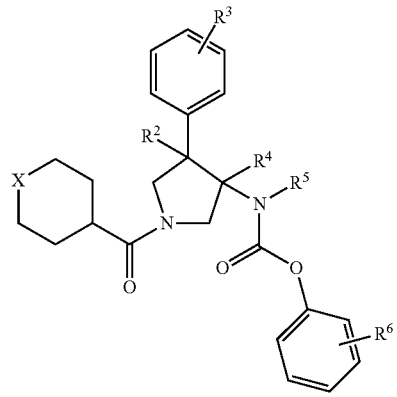

Ia wherein
X is NR or O;
R is —C(O)-lower alkyl, —C(O)-cycloalkyl substituted by lower alkyl, cycloalkyl or is phenyl, pyridinyl or pyridazinyl, wherein phenyl, pyridinyl and pyridazinyl are each optionally substituted by lower alkyl, lower alkoxy, cyano, —C(O)-lower alkyl, halogen or lower alkyl substituted by halogen;
R² is hydrogen or lower alkyl;
R³ is hydrogen, halogen, cyano, lower alkyl or lower alkyl substituted by halogen;
R⁴ is hydrogen or lower alkyl; wherein R² and R⁴ are not simultaneously hydrogen or lower alkyl;
R⁵ is lower alkyl; and
R⁶ is halogen, hydroxy, lower alkyl, lower alkoxy, lower alkyl substituted by halogen, S(O)₂-lower alkyl or cyano;
or a pharmaceutically suitable acid addition salt thereof.

An embodiment of this group of compounds are compounds wherein X is NR, for example the following compounds rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester;

rac-[(3R,4S)-4-(4-Chloro-phenyl)-1-(1-cyclohexyl-piperidine-4-carbonyl)-3-methyl-pyrrolidin-3-yl]-methyl-carbamic acid 4-fluoro-phenyl ester;

rac-[(3R,4S)-1-(1-Acetyl-piperidine-4-carbonyl)-4-(4-chloro-phenyl)-3-methyl-pyrrolidin-3-yl]-methyl-carbamic acid 4-fluoro-phenyl ester;

rac-{(3R,4S)-4-(4-Chloro-phenyl)-3-methyl-1-[1-(1-methyl-cyclopropanecarbonyl)-piperidine-4-carbonyl]-pyrrolidin-3-yl}-methyl-carbamic acid 4-fluoro-phenyl ester;

rac-[(3R,4S)-4-(4-Chloro-phenyl)-3-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3R,4S)-4-(4-Chloro-phenyl)-1-(5'-cyano-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-{(3R,4S)-4-(4-Chloro-phenyl)-1-[1-(4-cyano-phenyl)-piperidine-4-carbonyl]-3-methyl-pyrrolidin-3-yl}-methyl-carbamic acid 4-fluoro-phenyl ester;

rac-[(3R,4S)-1-(5'-Acetyl-3,4,5,6-tetrahydro-2H-[1,2']bipyridinyl-4-carbonyl)-4-(4-chloro-phenyl)-3-methyl-pyrrolidin-3-yl]-methyl-carbamic acid 4-fluoro-phenyl ester;

rac-[(3R,4S)-4-(4-Chloro-phenyl)-1-(5'-fluoro-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-[(3R,4S)-4-(4-Chloro-phenyl)-1-(5'-chloro-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-[(3R,4S)-4-(4-Chloro-phenyl)-3-methyl-1-(5'-trifluoromethyl-3,4,5,6-tetrahydro-2H-[1,2']bipyridinyl-4-carbonyl)-pyrrolidin-3-yl]-methyl-carbamic acid 4-fluorophenyl ester;

rac-[(3R,4S)-4-(4-Chloro-phenyl)-1-(6'-cyano-3,4,5,6-tetrahydro-2H-[1,3']bipyridinyl-4-carbonyl)-3-methyl-pyrrolidin-3-yl]-methyl-carbamic acid 4-fluoro-phenyl ester;

rac-{(3R,4S)-4-(4-Chloro-phenyl)-1-[1-(6-methoxy-pyridazin-3-yl)-piperidine-4-carbonyl]-3-methyl-pyrrolidin-3-yl}-methyl-carbamic acid 4-fluoro-phenyl ester;

rac-{(3S,4R)-4-(4-Chloro-phenyl)-4-methyl-1-[1-(1-methyl-cyclopropanecarbonyl)-piperidine-4-carbonyl]-pyrrolidin-3-yl}-methyl-carbamic acid 4-fluoro-phenyl ester;

rac-{(3S,4R)-4-(4-Chloro-phenyl)-1-[1-(4-cyano-phenyl)-piperidine-4-carbonyl]-4-methyl-pyrrolidin-3-yl}-methyl-carbamic acid 4-fluoro-phenyl ester;

rac-[(3S,4R)-4-(4-Chloro-phenyl)-1-(5'-fluoro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-1-(1-isobutyryl-piperidine-4-carbonyl)-4-methyl-pyrrolidin-3-yl]-methyl-carbamic acid 4-fluoro-phenyl ester;

[(3S,4R)-4-(4-Chloro-phenyl)-1-(1-cyclohexyl-piperidine-4-carbonyl)-4-methyl-pyrrolidin-3-yl]-methyl-carbamic acid 4-fluoro-phenyl ester;

rac-[(3S,4R)-1-(1-Acetyl-piperidine-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-4-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(5'-cyano-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-1-(5'-Acetyl-3,4,5,6-tetrahydro-2H-[1,2']bipyridinyl-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-1-(5'-chloro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-4-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(6'-cyano-3,4,5,6-tetrahydro-2H-[1,3']bipyridinyl-4-carbonyl)-4-methyl-pyrrolidin-3-yl]-methyl-carbamic acid 4-fluoro-phenyl ester and rac-{(3S    ,4R)-4-(4-Chloro-phenyl)-1-[1-(6-methoxy-pyridazin-3-yl)-piperidine-4-carbonyl]-4-methyl-pyrrolidin-3-yl}-methyl-carbamic acid 4-fluoro-phenyl ester.

A further embodiment of the invention provides compounds of formula Ia, wherein X is O, for example the following compounds:

rac-[(3R,4S)-4-(4-Chloro-phenyl)-3-methyl-1-(tetrahydro-pyran-4-carbonyl)-pyrrolidin-3-yl]-methyl-carbamic acid 4-fluoro-phenyl ester and rac-[(3S,4R)-4-(4-Chloro-phenyl)-4-methyl-1 -(tetrahydro-pyran-4-carbonyl)-pyrrolidin-3-yl]-methyl-carbamic acid 4-fluoro-phenyl ester.

A further embodiment of the invention provides compounds of formula Ib,

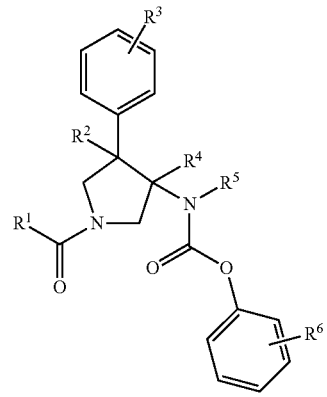

Ib wherein $R^1$ is phenyl, pyridinyl or pyridazinyl, wherein phenyl, pyridinyl and pyridazinyl are each optionally substituted by cyano, lower alkyl, halogen-substituted phenyl, lower alkyl-substituted [1,2,4]oxadiazol-3-yl or by 2-oxo-piperidin-1-yl;

$R^2$ is hydrogen or lower alkyl;

$R^3$ is hydrogen, halogen, cyano, lower alkyl or lower alkyl substituted by halogen;

$R^4$ is hydrogen or lower alkyl; wherein $R^2$ and $R^4$ are not simultaneously hydrogen or lower alkyl;

$R^5$ is lower alkyl; and $R^6$ is halogen, hydroxy, lower alkyl, lower alkoxy, lower alkyl substituted by halogen, $S(O)_2$-lower alkyl or cyano;

or a pharmaceutically suitable acid addition salt thereof.

A group of compounds of formula Ib are, for example, the following compounds:

rac-[(3R,4S)-4-(4-Chloro-phenyl)-1-(4-cyano-benzoyl)-3-methyl-pyrrolidin-3-yl]-methyl-carbamic acid 4-fluoro-phenyl ester;

rac-[(3R,4S)-4-(4-Chloro-phenyl)-3-methyl-1-(6-methyl-pyridazine-4-carbonyl)-pyrrolidin-3-yl]-methyl-carbamic acid 4-fluoro-phenyl ester;

rac-[(3R,4S)-4-(4-Chloro-phenyl)-1-(6-cyano-pyridine-3-carbonyl)-3-methyl-pyrrolidin-3-yl]-methyl-carbamic acid 4-fluoro-phenyl ester;

rac-[(3R,4S)-4-(4-Chloro-phenyl)-1-(4'-fluoro-biphenyl-4-carbonyl)-3-methyl-pyrrolidin-3-yl]-methyl-carbamic acid 4-fluoro-phenyl ester;

rac-{(3R,4S)-4-(4-Chloro-phenyl)-3-methyl-1-[4-(5-methyl-[1,2,4]oxadiazol-3-yl)-benzoyl]-pyrrolidin-3-yl}-methyl-carbamic acid 4-fluoro-phenyl ester;

rac-{(3R,4S)-4-(4-Chloro-phenyl)-3-methyl-1-[4-(2-oxo-piperidin-1    -yl)-benzoyl]-pyrrolidin-3-yl}-methyl-carbamic acid 4-fluoro-phenyl ester;

rac-[(3S,4R)-4-(4-Chloro-phenyl)-1-(4-cyano-benzoyl)-4-methyl-pyrrolidin-3-yl]-methyl-carbamic acid 4-fluoro-phenyl ester and rac-{(3S,4R)-4-(4-Chloro-phenyl)-4-methyl-1-[4-(2-oxo-piperidin-1    -yl)-benzoyl]-pyrrolidin-3-yl}-methyl-carbamic acid 4-fluoro-phenyl ester.

The present compounds of formula I and their pharmaceutically acceptable salts can be prepared by methods known in the art, for example, by processes described below, which process comprises deprotecting a compound of formula

IV

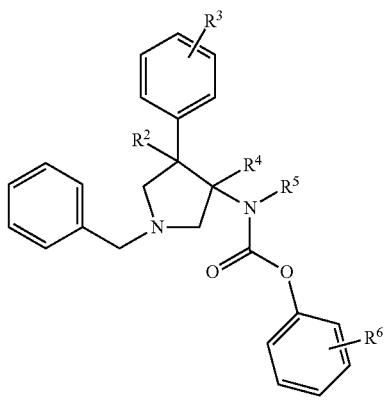

in the usual manner and coupling with a compound of formula

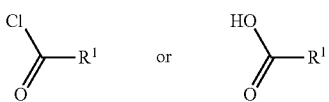

to obtain a compound of formula

I

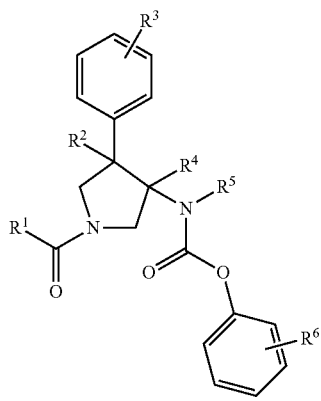

wherein the definitions $R^1$, $R^2$, $R^3$, $R^4$, $R^5$ and $R^6$ are as described above, and, if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following scheme 1 and in the description for preparation of the specific compounds 1-36. The skills required for carrying out the reaction and purification of the resulting products are known to those skilled in the art. The substituents and indices used in the following description of the processes have the significance given herein before unless indicated to the contrary.

GENERAL EXPERIMENTAL PART

Scheme 1

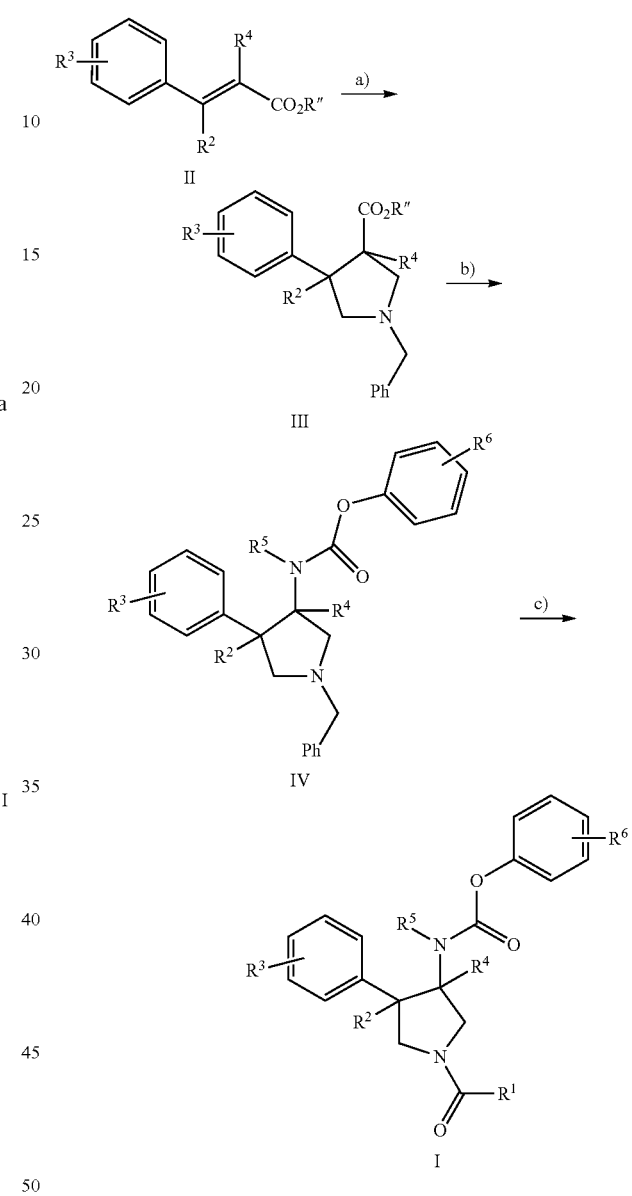

wherein $R^1$-$R^6$ are as defined above and R" is Me, Et and the like (any suitable ester functionality).

The following scheme 1 describes the processes for the preparation of compounds of formula I in more detail. The starting material of formula II is a known compound or can be prepared according to methods known in the art.

According to scheme 1, the 3,4-disubstituted pyrrolidine III is prepared via a stereo specific 1,3-dipolar cycloaddition between the unsaturated ester derivative II and the azomethine ylide generated in situ from the N-(methoxymethyl)-N-(phenylmethyl)-N-(trimethylsilyl) methylamine in the presence of a catalytic amount of acid, such as TFA. Curtius rearrangement of the liberated acid is affected using standard conditions for example diphenylphosphoryl azide in tert.-butanol obtaining the respective Boc protected amine. This is conveniently alkylated at the free NH position with alkyl halides in the presence of a base such as NEt$_3$ or NaH. Subsequently the Boc-protecting group is cleaved under acidic conditions with acids such as TFA or HCl. The amino moiety is transformed towards the respective pyrrolidine derivative IV with isocyanates or respectively with a phosgene equivalent and the respective alcohol or amine. Selective N-debenzylation is then carried out using several known procedures which are compatible with the substitution patterns of the aromatic rings to afford the free pyrrolidine. Finally, derivatives I are prepared via a coupling with a suitable acid chloride or carboxylic acide.

The compounds of formula I and their pharmaceutically usable addition salts possess valuable pharmacological properties. Specifically, compounds of the present invention have a good affinity to the NK3 receptor.

The compounds were investigated in accordance with the test given hereinafter.

[$^3$11]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10µM SB222200 for both radioligands. The radioactivity on the filter was counted (5 min) on a Packard Top-count microplate scintillation counter with quenching correction after addition of 45 µl of microscint 40 (Canberra Packard S.A., Zürich, Switzerland) and shaking for 1 h. Inhibition curves were fitted according to the Hill equation: $y=100/(1+(x/IC_{50})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i = IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

The results of hNK-3 receptor affinity for representative compounds are shown in the following Table 1.

TABLE 1

| Example | Ki (uM) hNK3 |
| --- | --- |
| 1 | 0.0105 |
| 2 | 0.0201 |
| 3 | 0.0678 |
| 4 | 0.0116 |
| 5 | 0.0864 |

TABLE 1-continued

| Example | Ki (uM) hNK3 |
| --- | --- |
| 6 | 0.0649 |
| 7 | 0.005 |
| 8 | 0.013 |
| 9 | 0.0021 |
| 10 | 0.0038 |
| 11 | 0.0045 |
| 12 | 0.0076 |
| 13 | 0.01 |
| 14 | 0.0774 |
| 15 | 0.0115 |
| 16 | 0.2997 |
| 17 | 0.0354 |
| 18 | 0.0028 |
| 19 | 0.0129 |
| 20 | 0.2757 |
| 21 | 0.0319 |
| 22 | 0.0105 |
| 23 | 0.0435 |
| 24 | 0.0392 |
| 25 | 0.0915 |
| 26 | 0.6294 |
| 27 | 0.051 |
| 28 | 0.3476 |
| 29 | 0.0245 |
| 30 | 0.0053 |
| 31 | 0.0081 |
| 32 | 0.0099 |
| 33 | 0.02 |
| 34 | 0.0029 |
| 35 | 0.0213 |
| 36 | 0.9973 |

The compounds of formula I as well as their pharmaceutically usable acid addition salts can be used as for the treatment of CNS disorders, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples 1-36 illustrate the present invention without limiting it. All temperatures are given in degrees Celsius.

Example 1 rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester

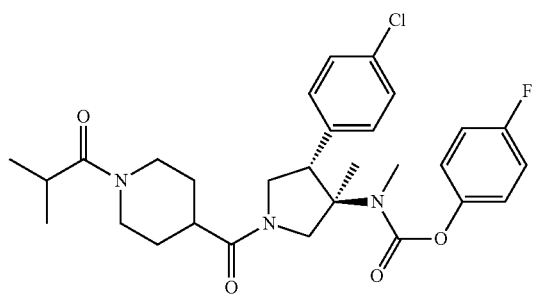 [SMILES: CC(C)C(=O)N1CCC(C(=O)N2C[C@H](c3ccc(Cl)cc3)[C@@](C)(N(C)C(=O)Oc3ccc(F)cc3)C2)CC1]

a) rac-(3R,4R)-1-Benzyl-4-(4-chloro-phenyl)-3-methyl-pyrrolidine-3-carboxylic acid methyl ester

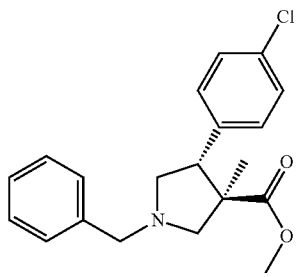 [SMILES: COC(=O)[C@@]1(C)CN(Cc2ccccc2)C[C@@H]1c1ccc(Cl)cc1]

A mixture of 8.8 g (41.8 mmol) (E)-methyl 3-(4-chlorophenyl)-2-methylacrylate (freshly distilled) 0.476 g (4.18 mmol) TFA, and 12.4 g (52 2 mmol) N-(methoxymethyl)-N-(trimethylsilylmethyl)benzylamine in 100 mL DCM was stirred at 0-5° C. for 1 h and at room temperature. NEt₃ was added and the mixture was concentrated. The residue was purified by column chromatography on silica eluting with a gradient formed from ethyl acetate and heptane to yield after evaporation of the product containing fractions 7.55 g (53%) of the title compound as colorless oil. MS m/e: 344.1 [M+H]⁺.

b) rac-(3R,4R)-1-Benzyl-4-(4-chloro-phenyl)-3-methyl-pyrrolidine-3-carboxylic acid

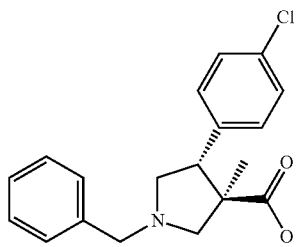 [SMILES: C[C@]1(C(=O)O)CN(Cc2ccccc2)C[C@@H]1c1ccc(Cl)cc1]

A mixture of 7.7 g (22.4 mmol) rac-(3R,4R)-1-Benzyl-4-(4-chloro-phenyl)-3-methyl-pyrrolidine-3-carboxylic acid methyl ester and 1.41 g (22.4 mmol) LiOH.H$_2$O in 80 mL THF, 80 mL water and 8 mL methanol was heated to reflux over night. The organic solvents were removed under vacuum and the pH was adjusted to 4-5 by addition of HCl aq. (1N). The mixture was extracted with ethyl acetate/THF (2:1) and the combined organic layers were washed with brine, dried with Na$_2$SO$_4$, filtered off and evaporated to dryness. The residue was dried to yield 7.2 g (97%) of the title compound as light brown foam. MS m/e: 328.3 [M+H]$^+$.

c) rac-[(3R,4S)-1-Benzyl-4-(4-chloro-phenyl)-3-methyl-pyrrolidin-3-yl]-carbamic acid tert-butyl ester

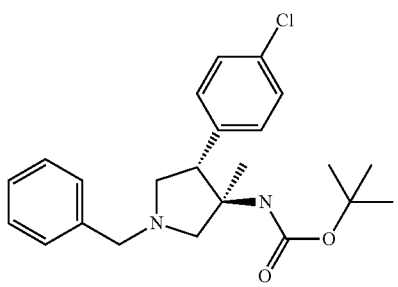 [SMILES: CC(C)(C)OC(=O)N[C@@]1(C)CN(Cc2ccccc2)C[C@@H]1c1ccc(Cl)cc1]

A mixture of 5.6 g (17 mmol) rac-(3R,4R)-1-Benzyl-4-(4-chloro-phenyl)-3-methyl-pyrrolidine-3-carboxylic acid, 2.4 g (18.7 mmol) DIPEA and 5.14 g (18.7 mmol) diphenylphosphoryl azide in 120 mL tert.-butanol was heated to reflux over night. The mixture was concentrated under vacuum and purified by column chromatography on silica eluting with a gradient formed from heptane and ethyl acetate to yield after evaporation of the product containing fractions 4.63 g (68%) of the title compound as yellow viscous oil. MS m/e: 401.3 [M+H]$^+$.

d) rac-[(3R,4S)-1-Benzyl-4-(4-chloro-phenyl)-3-methyl-pyrrolidin-3-yl]-methyl-carbamic acid 4-fluoro-phenyl ester

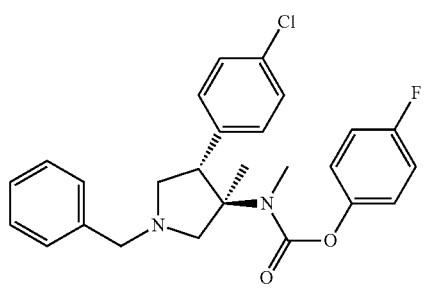 [SMILES: CN(C(=O)Oc1ccc(F)cc1)[C@@]1(C)CN(Cc2ccccc2)C[C@@H]1c1ccc(Cl)cc1]

A mixture of 2.49 g (6.21 mmol) rac-tert-butyl (3R,4S)-1-benzyl-4-(4-chlorophenyl)-3-methylpyrrolidin-3-ylcarbamate, 0.836 g (7.45 mmol) potassium tert.-butoxide and 0.98 g (7.76 mmol) dimethyl sulfate in 80 mL DMSO was stirred at room temperature for 1 h. The mixture was poured onto ice-water and extracted with TBME. The combined organic layers were washed with brine, died with Na$_2$SO$_4$, filtered off and evaporated to dryness. The residue was dissolved in 40 mL DCM and 7.68 g (67.3 mmol) TFA was added. The mixture was stirred at room temperature over night and ice-water was added. The pH was adjusted to 12 and the organic layer was washed with brine. The aqueous layer was extracted with DCM and the combined organic layers were dried with Na$_2$SO$_4$, filtered off and evaporated to dryness. The residue was dissolved in 40 mL DCM and 1.04 g (8.08 mmol) DIPEA and at −15° C. 1.29 g (7.41 mmol) 4-fluorophenyl chloroformate was added. The mixture was stirred to 0° C. during 2 h and concentrated under vacuum the residue was purified by column chromatography on silica eluting with a gradient formed from heptane and ethyl acetate to yield after evaporation of the product containing fractions 1.68 g (59%) of the title compound as light brown viscous oil. MS m/e: 453.1 [M+H]$^+$.

e) rac-[(3R,4S)-4-(4-Chloro-phenyl)-3-methyl-pyrrolidin-3-yl]-methyl-carbamic acid 4-fluoro-phenyl ester

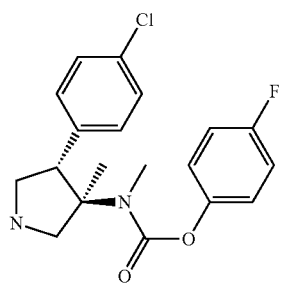 [SMILES: CN(C(=O)Oc1ccc(F)cc1)[C@@]1(C)CNC[C@@H]1c1ccc(Cl)cc1]

A mixture of 1.65 g (3.64 mmol) rac-[(3R,4S)-1-Benzyl-4-(4-chloro-phenyl)-3-methyl-pyrrolidin-3-yl]-methyl-carbamic acid 4-fluoro-phenyl ester, 0.75 g (5.83 mmol) DIPEA and 0.78 g (5.46 mmol) 1-chloroethyl chloroformate in 40 mL toluene was stirred at room temperature and evaporated to dryness. The residue was taken up in 40 mL methanol and stirred for 2 h at room temperature and evaporated to dryness to yield the crude title compound which was used without further purification in the consecutive step.

f) rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester A mixture of 34 mg (0.093 mmol) rac-4-fluorophenyl (3R,4S)-4-(4-chlorophenyl)-3-methylpyrrolidin-3-yl(methyl)carbamate, 14.9 mg (0.075)mmol 1-isobutyrylpiperidine-4-carboxylic acid, 34.2 (0.09 mmol) HATU and 58 mg (0.45 mmol) DIPEA in 2 mL DMF was shaken for 3 h at room temperature. The mixture was subjected to purification by preparative HPLC on reversed phase eluting with a gradient formed from acetonitrile, water and NEt$_3$ to yield after evaporation of the product containing fractions 26.8 (66%) of the title compound as light yellow viscous oil. MS m/e: 544.2 [M+H]$^+$.

Example 2 rac-[(3R,4S)-4-(4-Chloro-phenyl)-1-(1-cyclohexyl-piperidine-4-carbonyl)-3-methyl-pyrrolidin-3-yl]-methyl-carbamic acid 4-fluoro-phenyl ester

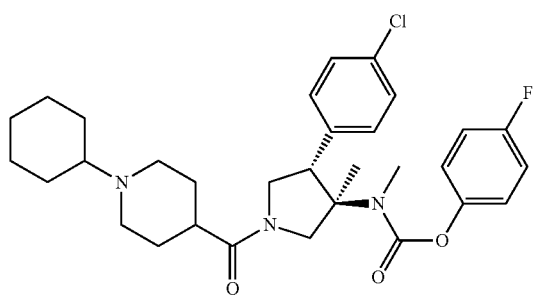 [SMILES: CN(C(=O)Oc1ccc(F)cc1)[C@@]1(C)CN(C(=O)C2CCN(C3CCCCC3)CC2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-cyclohexylpiperidine-4-carboxylic acid as yellow viscous oil. MS m/e: 556.3 [M+H]$^+$.

Example 3 rac-[(3R,4S)-4-(4-Chloro-phenyl)-1-(4-cyano-benzoyl)-3-methyl-pyrrolidin-3-yl]-methyl-carbamic acid 4-fluoro-phenyl ester

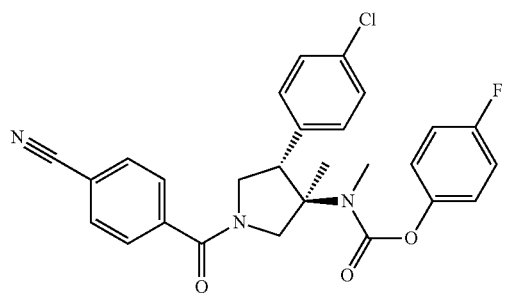

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 4-cyanobenzoic acid as off-white solid. MS m/e: 492.2 [M+H]$^+$.

Example 4 rac-[(3R,4S)-1-(1-Acetyl-piperidine-4-carbonyl)-4-(4-chloro-phenyl)-3-methyl-pyrrolidin-3-yl]-methyl-carbamic acid 4-fluoro-phenyl ester

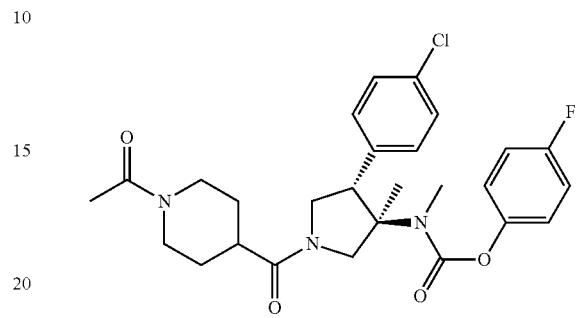

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-acetylpiperidine-4-carboxylic acid as off-white solid. MS m/e: 516.2 [M+H]$^+$.

Example 5 rac-[(3R,4S)-4-(4-Chloro-phenyl)-3-methyl-1-(tetrahydro-pyran-4-carbonyl)-pyrrolidin-3-yl]-methyl-carbamic acid 4-fluoro-phenyl ester

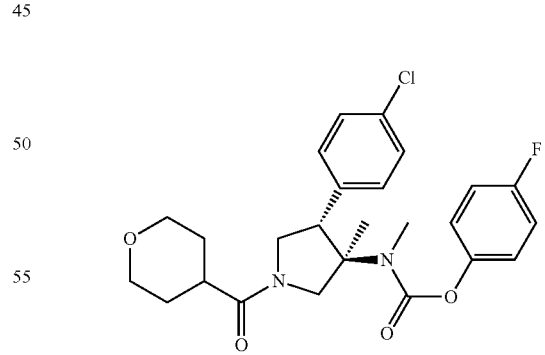

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and tetrahydro-2H-pyran-4-carboxylic acid as off-white solid. MS m/e: 475.2 [M+H]⁺.

Example 6 rac-[(3R,4S)-4-(4-Chloro-phenyl)-3-methyl-1-(6-methyl-pyridazine-4-carbonyl)-pyrrolidin-3-yl]-methyl-carbamic acid 4-fluoro-phenyl ester

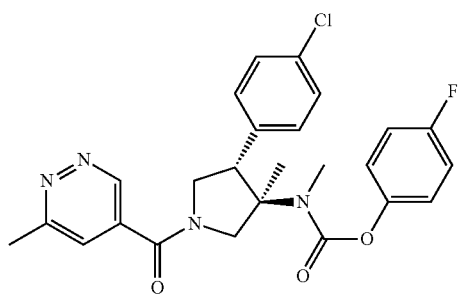 [SMILES: Cc1cc(C(=O)N2C[C@H](c3ccc(Cl)cc3)[C@@](C)(N(C)C(=O)Oc3ccc(F)cc3)C2)cnn1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 6-methylpyridazine-4-carboxylic acid as off-white solid. MS m/e: 483.4 [M+H]⁺.

Example 7 rac-{(3R,4S)-4-(4-Chloro-phenyl)-3-methyl-1-[1-(1-methyl-cyclopropanecarbonyl)-piperidine-4-carbonyl]-pyrrolidin-3-yl}-methyl-carbamic acid 4-fluoro-phenyl ester

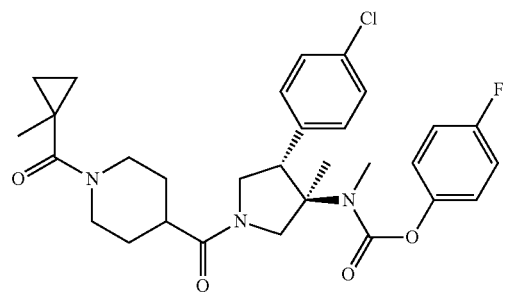 [SMILES: CN(C(=O)Oc1ccc(F)cc1)[C@@]1(C)CN(C(=O)C2CCN(C(=O)C3(C)CC3)CC2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(1-methylcyclopropanecarbonyl)piperidine-4-carboxylic acid as off-white solid. MS m/e: 556.3 [M+H]⁺.

Example 8 rac-[(3R,4S)-4-(4-Chloro-phenyl)-3-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester

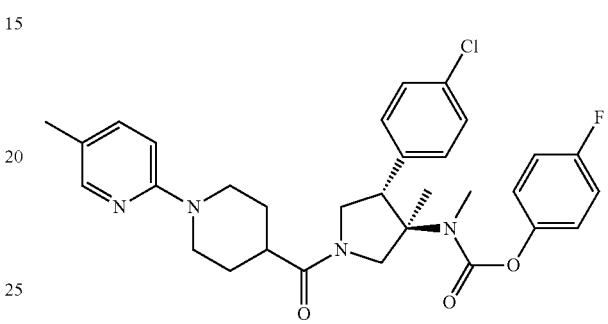

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(5-methylpyridin-2-yl)piperidine-4-carboxylic acid as off-white solid. MS m/e: 565.3 [M+H]⁺.

Example 9 rac-[(3R,4S)-4-(4-Chloro-phenyl)-1-(5'-cyano-3,4,5,6-tetrahydro-2H-[1,2']bipyridinyl-4-carbonyl)-3-methyl-pyrrolidin-3-yl]-methyl-carbamic acid 4-fluoro-phenyl ester

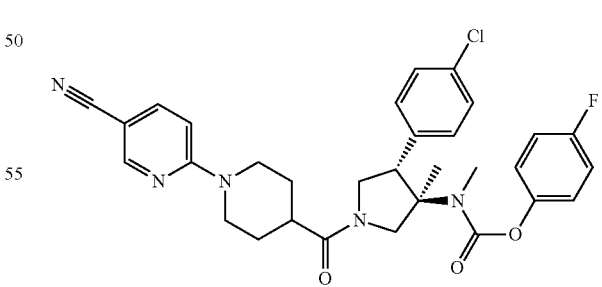

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(5-cyanopyridin-2-yl)piperidine-4-carboxylic acid as off-white solid. MS m/e: 576.3 [M+H]⁺.

Example 10 rac-{(3R,4S)-4-(4-Chloro-phenyl)-1-[1-(4-cyano-phenyl)-piperidine-4-carbonyl]-3-methyl-pyrrolidin-3-yl}-methyl-carbamic acid 4-fluoro-phenyl ester

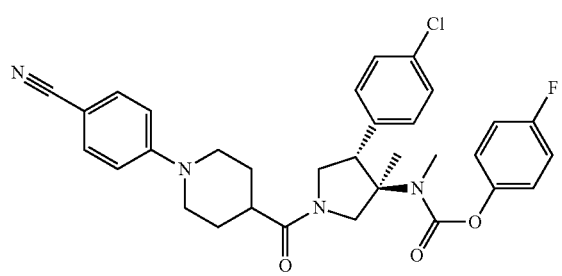

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(4-cyanophenyl)piperidine-4-carboxylic acid as off-white solid. MS m/e: 575.4 [M+H]⁺.

Example 11 rac-[(3R,4S)-1-(5'-Acetyl-3,4,5,6-tetrahydro-2H-[1,2']bipyridinyl-4-carbonyl)-4-(4-chloro-phenyl)-3-methyl-pyrrolidin-3-yl]-methyl-carbamic acid 4-fluoro-phenyl ester

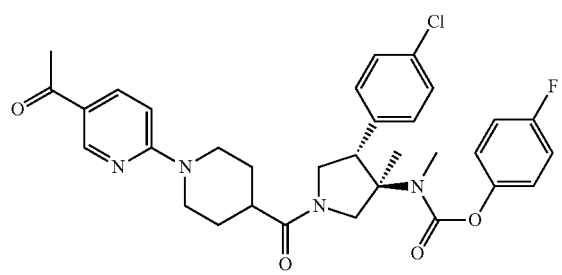 [SMILES: CC(=O)c1ccc(N2CCC(C(=O)N3C[C@H](c4ccc(Cl)cc4)[C@@](C)(N(C)C(=O)Oc4ccc(F)cc4)C3)CC2)nc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(5-acetylpyridin-2-yl)piperidine-4-carboxylic acid as off-white solid. MS m/e: 593.5 [M+H]⁺.

Example 12 rac-[(3R,4S)-4-(4-Chloro-phenyl)-1-(5'-fluoro-3,4,5,6-tetrahydro-2H-[1,2']bipyridinyl-4-carbonyl)-3-methyl-pyrrolidin-3-yl]-methyl-carbamic acid 4-fluoro-phenyl ester

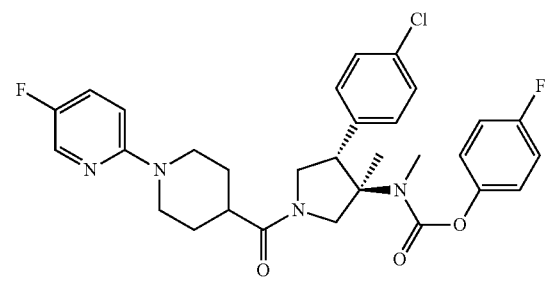 [SMILES: CN(C(=O)Oc1ccc(F)cc1)[C@@]1(C)CN(C(=O)C2CCN(c3ccc(F)cn3)CC2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(5-fluoropyridin-2-yl)piperidine-4-carboxylic acid as off-white solid. MS m/e: 569.3 [M+H]⁺.

Example 13 rac-[(3R,4S)-4-(4-Chloro-phenyl)-1-(5'-chloro-3,4,5,6-tetrahydro-2H-[1,2']bipyridinyl-4-carbonyl)-3-methyl-pyrrolidin-3-yl]-methyl-carbamic acid 4-fluoro-phenyl ester

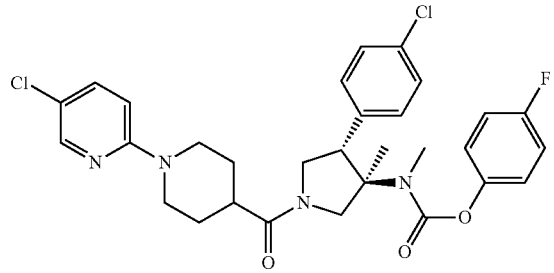 [SMILES: CN(C(=O)Oc1ccc(F)cc1)[C@@]1(C)CN(C(=O)C2CCN(c3ccc(Cl)cn3)CC2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(5-chloropyridin-2-yl)piperidine-4-carboxylic acid as yellow viscous oil. MS m/e: 585.2 [M+H]+.

Example 14 rac-[(3R,4S)-4-(4-Chloro-phenyl)-1-(6-cyano-pyridine-3-carbonyl)-3-methyl-pyrrolidin-3-yl]-methyl-carbamic acid 4-fluoro-phenyl ester

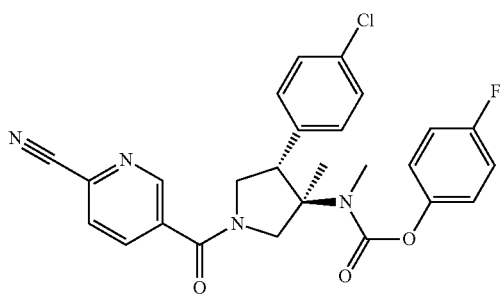 [SMILES: CN(C(=O)Oc1ccc(F)cc1)[C@@]1(C)CN(C(=O)c2ccc(C#N)nc2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 6-cyanonicotinic acid as off-white solid. MS m/e: 493.2 [M+H]+.

Example 15 rac-[(3R,4S)-4-(4-Chloro-phenyl)-3-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester

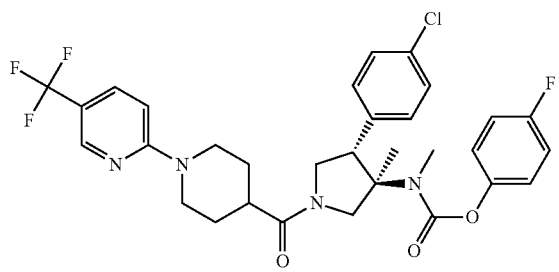 [SMILES: CN(C(=O)Oc1ccc(F)cc1)[C@@]1(C)CN(C(=O)C2CCN(c3ccc(C(F)(F)F)cn3)CC2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(5-(trifluoromethyl)pyridin-2-yl)piperidine-4-carboxylic acid as off-white solid. MS m/e: 619.3 [M+H]+.

Example 16 rac-[(3R,4S)-4-(4-Chloro-phenyl)-1-(4'-fluoro-biphenyl-4-carbonyl)-3-methyl-pyrrolidin-3-yl]-methyl-carbamic acid 4-fluoro-phenyl ester

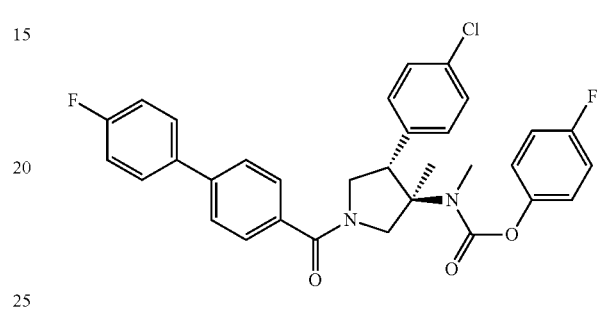

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 4'-fluorobiphenyl-4-carboxylic acid as yellow viscous oil. MS m/e: 561.3 [M+H]+.

Example 17 rac-{(3R,4S)-4-(4-Chloro-phenyl)-3-methyl-1-[4-(5-methyl-[1,2,4]oxadiazol-3-yl)-benzoyl]-pyrrolidin-3-yl}-methyl-carbamic acid 4-fluoro-phenyl ester

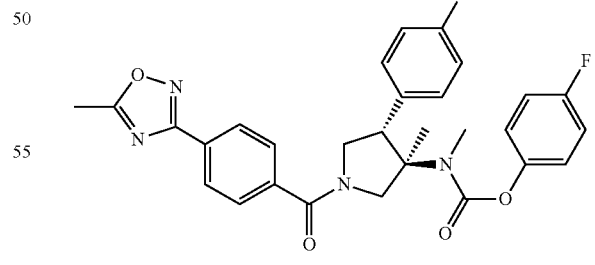

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 4-(5-methyl-1,2,4-oxadiazol-3-yl)benzoic acid as off-white solid. MS m/e: 549.3 [M+H]+.

Example 18 rac-[(3R,4S)-4-(4-Chloro-phenyl)-1-(6'-cyano-3,4,5, 6-tetrahydro-2H-[1,3']bipyridinyl-4-carbonyl)-3-methyl-pyrrolidin-3-yl]-methyl-carbamic acid 4-fluoro-phenyl ester

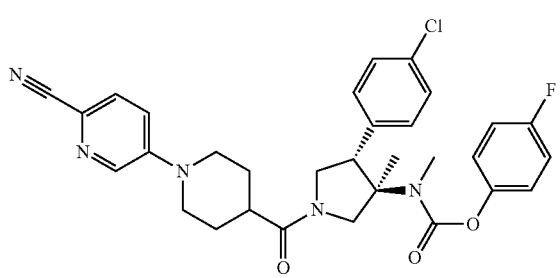 [SMILES: CN(C(=O)Oc1ccc(F)cc1)[C@@]1(C)CN(C(=O)C2CCN(c3ccc(C#N)nc3)CC2)C[C@@H]1c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 6'-Cyano-3,4,5,6-tetrahydro-2H-[1,3']bipyridinyl-4-carboxylic acid as off-white solid. MS m/e: 576.3 [M+H]+.

Example 19 rac-{(3R,4S)-4-(4-Chloro-phenyl)-1-[1-(6-methoxy-pyridazin-3-yl)-piperidine-4-carbonyl]-3-methyl-pyrrolidin-3-yl}-methyl-carbamic acid 4-fluoro-phenyl ester

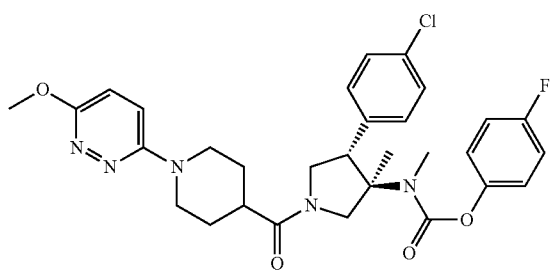 [SMILES: COc1ccc(N2CCC(C(=O)N3C[C@H](c4ccc(Cl)cc4)[C@@](C)(N(C)C(=O)Oc4ccc(F)cc4)C3)CC2)nn1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 1-(6-methoxypyridazin-3-yl)piperidine-4-carboxylic acid as off-white solid. MS m/e: 582.2 [M+H]+.

Example 20 rac-{(3R,4S)-4-(4-Chloro-phenyl)-3-methyl-1-[4-(2-oxo-piperidin-1-yl)-benzoyl]-pyrrolidin-3-yl}-methyl-carbamic acid 4-fluoro-phenyl ester

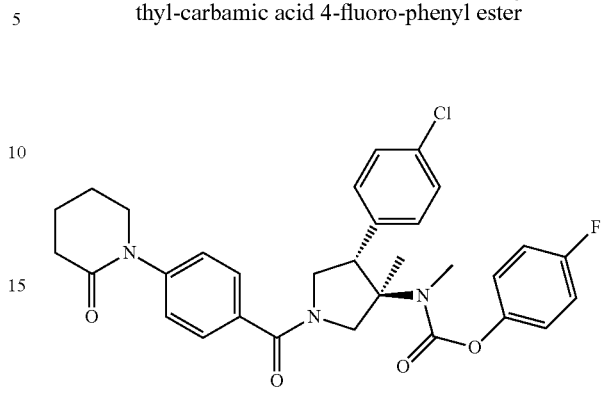

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-4-fluorophenyl (3R,4S)-4-(4-chlorophenyl)-3-methylpyrrolidin-3-yl(methyl)carbamate and 4-(2-oxopiperidin-1-yl)benzoic acid as off-white solid. MS m/e: 564.3 [M+H]+.

Example 21 rac-{(3S,4R)-4-(4-Chloro-phenyl)-4-methyl-1-[1-(1-methyl-cyclopropanecarbonyl)-piperidine-4-carbonyl]-pyrrolidin-3-yl}-methyl-carbamic acid 4-fluoro-phenyl ester

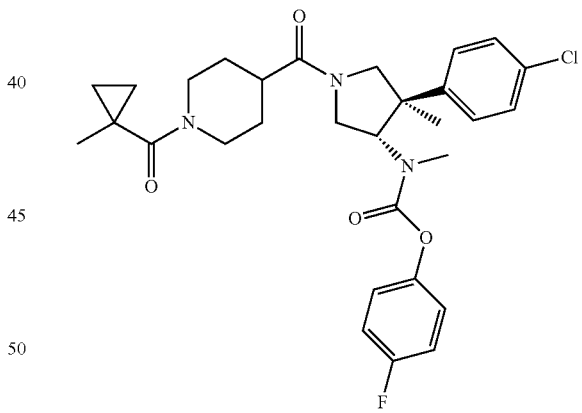

a) rac-(3S,4R)-1-Benzyl-4-(4-chloro-phenyl)-4-methyl-pyrrolidine-3-carboxylic acid methyl ester

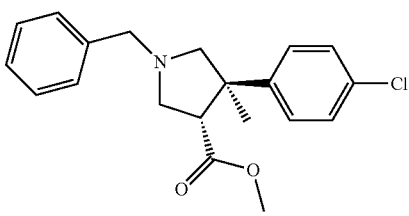 [SMILES: COC(=O)[C@@H]1CN(Cc2ccccc2)C[C@@]1(C)c1ccc(Cl)cc1]

A mixture of 11.7 g (55 5 mmol) (E)-methyl 3-(4-chlorophenyl)but-2-enoate (Organic Letters 2008, 2131-2134), 16.5 g (69 4 mmol) N-(methoxymethyl)-N-(trimethylsilylmethyl)benzylamine and 0.63 g (5.5 mmol) TFA in 30 mL DCM was stirred at 0-5° C. for 1 h and then at room temperature over night. The mixture was neutralised with NEt$_3$ and evaporated. The residue was taken up on isolute and purified by column chromatography on silica eluting with a gradient formed from ethyl acetate and heptane. After evaporation of the product containing fractions 9.6 g (50%) of the title compounds was isolated as colorless oil. MS m/e: 344.1 [M+H]$^+$.

b) rac-(3S,4R)-1-Benzyl-4-(4-chloro-phenyl)-4-methyl-pyrrolidine-3-carboxylic acid

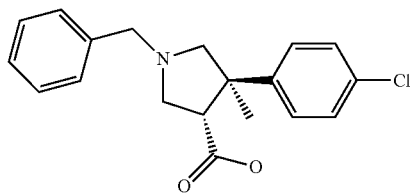 [SMILES: C[C@@]1(c2ccc(Cl)cc2)CN(Cc2ccccc2)C[C@H]1C(=O)O]

A mixture of 9.56 g (27.8 mmol) rac-(3S,4R)-1-Benzyl-4-(4-chloro-phenyl)-4-methyl-pyrrolidine-3-carboxylic acid methyl ester and 3.5 g (83.4 mmol) LiOH.H$_2$0 in 50 mL THF/50 mL water and 5 mL methanol was heated to reflux and stirred over night. The organic solvents were removed under vacuum and the aqueous phase was adjusted to pH=4-5 with 1N HCl aq. Water was decanted off the residue and THF was added. The mixture was diluted with ethyl acetate and washed with brine. The aqueous layer was back-extracted with ethyl acetate/THF (1:1) and the organic layers were evaporated to yield 8.9 g (97%) of the title compounds as off-white solid. MS m/e: 328.3 [M−H].

c) rac-[(3S,4R)-1-Benzyl-4-(4-chloro-phenyl)-4-methyl-pyrrolidin-3-yl]-carbamic acid tert-butyl ester

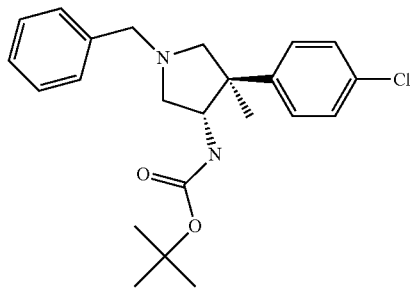 [SMILES: CC(C)(C)OC(=O)N[C@@H]1CN(Cc2ccccc2)C[C@@]1(C)c1ccc(Cl)cc1]

A mixture of 4.9 g (14 9 mmol) rac-(3S,4R)-1-Benzyl-4-(4-chloro-phenyl)-4-methyl-pyrrolidine-3-carboxylic acid, 4.5 g (16.3 mmol) diphenylphosphoryl azide and 2.1 g (16.3 mmol) DIPEA in 80 mL tert.-butanol was heated to reflux over night. The mixture was concentrated, taken up on isolute and subjected to purification by chromatography on silica eluting with a gradient formed from heptane and ethyl acetate to yield after evaporation of the product containing fractions 3.8 g (64%) of the title compound as light yellow viscous oil. MS m/e: 401.4 [M+H]$^+$.

d) rac-[(3S,4R)-1-Benzyl-4-(4-chloro-phenyl)-4-methyl-pyrrolidin-3-yl]-methyl-amine

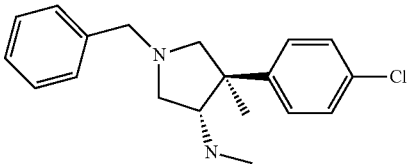 [SMILES: CN[C@@H]1CN(Cc2ccccc2)C[C@@]1(C)c1ccc(Cl)cc1]

A mixture of 2 g (4.99 mmol) rac-[(3S,4R)-1-Benzyl-4-(4-chloro-phenyl)-4-methyl-pyrrolidin-3-yl]-carbamic acid tert-butyl ester, 0.67 g (5.99 mmol) potassium tert.-butoxide and 0.786 (6.24 mmol) dimethyl sulfate in 40 mL DMSO was stirred for 1 h at room temperature. The mixture was poured on ice-water containing NaOH (1N) and extracted with TBME. The combined organic layers were washed with brine, dried with Na$_2$SO$_4$, filtered and evaporated. The residue was dissolved in 30 mL DCM, 5.69 g (49.9 mmol) TFA was added and the mixture was stirred at room temperature for 15 h. Ice-water was added and the pH was adjusted to 12 with NaOH aq. and stirred for 15 min The organic layer was separated and washed with brine and the aqueous layer was extracted with DCM. The combined organic layers were dried with Na$_2$SO$_4$, filtered and evaporated. The residue was taken up on isolute and subjected to purification by chromatography on silica eluting with a gradient formed from DCM, methanol and NEt$_3$ to yield after evaporation of the product containing fractions 0.83 g (53%) of the title compound as light yellow oil. MS m/e: 315.1 [M+H]$^+$.

e) rac-[(3S,4R)-1-Benzyl-4-(4-chloro-phenyl)-4-methyl-pyrrolidin-3-yl]-methyl-carbamic acid 4-fluoro-phenyl ester

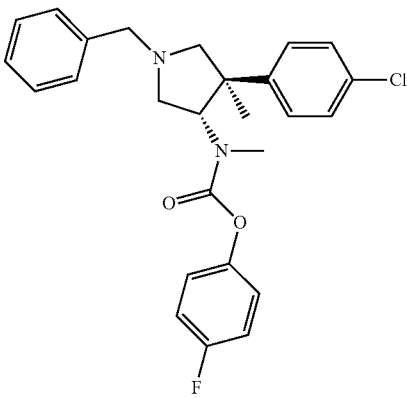 [SMILES: CN(C(=O)Oc1ccc(F)cc1)[C@@H]1CN(Cc2ccccc2)C[C@@]1(C)c1ccc(Cl)cc1]

In analogy to the procedure described for the synthesis of rac-[(3R,4S)-1-Benzyl-4-(4-chloro-phenyl)-3-methyl-pyrrolidin-3-yl]-methyl-carbamic acid 4-fluoro-phenyl ester (example 1, step d) the title compound was prepared from rac-[(3S,4R)-1-Benzyl-4-(4-chloro-phenyl)-4-methyl-pyrrolidin-3-yl]-methyl-amine and 4-fluorophenyl chlorocarbamate as colorless viscous oil. MS m/e: 452.3 [M+H]$^+$.

f) rac-[(3S,4R)-4-(4-Chloro-phenyl)-4-methyl-pyrrolidin-3-yl]-methyl-carbamic acid 4-fluoro-phenyl ester

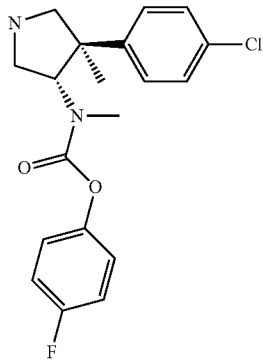 [SMILES: CN(C(=O)Oc1ccc(F)cc1)[C@@H]1CNC[C@@]1(C)c1ccc(Cl)cc1]

In analogy to the procedure described for the synthesis of rac-[(3R,4S)-4-(4-Chloro-phenyl)-3-methyl-pyrrolidin-3-yl]-methyl-carbamic acid 4-fluoro-phenyl ester (example 1, step e) the title compound was prepared from rac-[(3S,4R)-1-Benzyl-4-(4-chloro-phenyl)-4-methyl-pyrrolidin-3-yl]-methyl-carbamic acid 4-fluoro-phenyl ester though cleavage of the protecting group with 1-chloroethyl chloroformate/methanol and used without further purification in the subsequent step.

g) rac-{(3S,4R)-4-(4-Chloro-phenyl)-4-methyl-1-[1-(1-methyl-cyclopropanecarbonyl)-piperidine-4-carbonyl]-pyrrolidin-3-yl}-methyl-carbamic acid 4-fluoro-phenyl ester In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 4-(1-methylcyclopropanecarbonyl) cyclohexanecarboxylic acid as off-white solid. MS m/e: 556.2 [M+H]⁺.

Example 22 rac-{(3S,4R)-4-(4-Chloro-phenyl)-1-[1-(4-cyano-phenyl)-piperidine-4-carbonyl]-4-methyl-pyrrolidin-3-yl}-methyl-carbamic acid 4-fluoro-phenyl ester

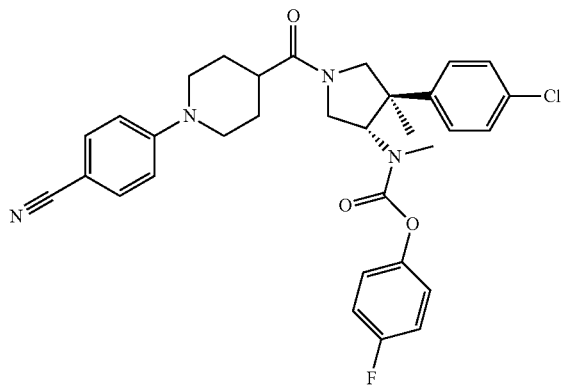 [SMILES: CN(C(=O)Oc1ccc(F)cc1)[C@@H]1CN(C(=O)C2CCN(c3ccc(C#N)cc3)CC2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(4-cyanophenyl)piperidine-4-carboxylic acid as off-white solid. MS m/e: 575.3 [M+H]⁺.

Example 23 rac-[(3S,4R)-4-(4-Chloro-phenyl)-1-(5'-fluoro-3,4,5,6-tetrahydro-2H-[1,2']bipyridinyl-4-carbonyl)-4-methyl-pyrrolidin-3-yl]-methyl-carbamic acid 4-fluoro-phenyl ester

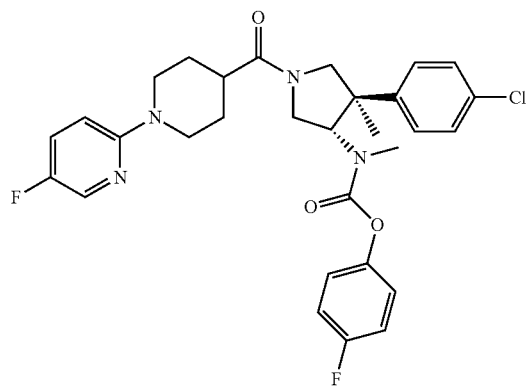 [SMILES: CN(C(=O)Oc1ccc(F)cc1)[C@@H]1CN(C(=O)C2CCN(c3ccc(F)cn3)CC2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(5-fluoropyridin-2-yl)piperidine-4-carboxylic acid as off-white solid. MS m/e: 569.2 [M+H]⁺.

Example 24 rac-[(3S,4R)-4-(4-Chloro-phenyl)-1-(1-isobutyryl-piperidine-4-carbonyl)-4-methyl-pyrrolidin-3-yl]-methyl-carbamic acid 4-fluoro-phenyl ester

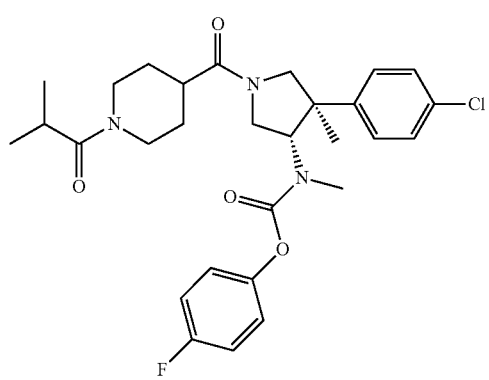 [SMILES: CC(C)C(=O)N1CCC(C(=O)N2C[C@@H](N(C)C(=O)Oc3ccc(F)cc3)[C@](C)(c3ccc(Cl)cc3)C2)CC1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-isobutyrylpiperidine-4-carboxylic acid as off-white solid. MS m/e: 544.2 [M+H]$^+$.

Example 25

[(3S,4R)-4-(4-Chloro-phenyl)-1-(1-cyclohexyl-piperidine-4-carbonyl)-4-methyl-pyrrolidin-3-yl]-methyl-carbamic acid 4-fluoro-phenyl ester

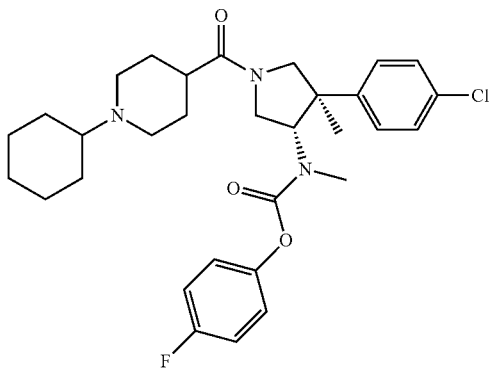 [SMILES: CN(C(=O)Oc1ccc(F)cc1)[C@@H]1CN(C(=O)C2CCN(C3CCCCC3)CC2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-cyclohexylpiperidine-4-carboxylic acid as light yellow viscous oil. MS m/e: 556.3 [M+H]$^+$.

Example 26 rac-[(3S,4R)-4-(4-Chloro-phenyl)-1-(4-cyano-benzoyl)-4-methyl-pyrrolidin-3-yl]-methyl-carbamic acid 4-fluoro-phenyl ester

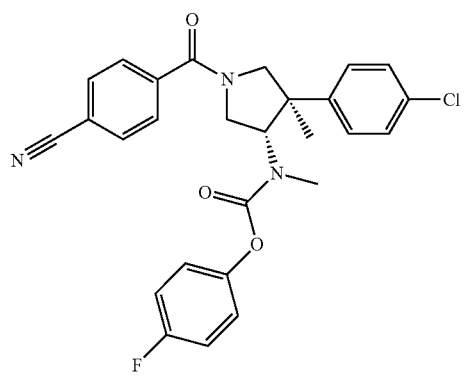 [SMILES: CN(C(=O)Oc1ccc(F)cc1)[C@@H]1CN(C(=O)c2ccc(C#N)cc2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 4-cyanobenzoic acid as off-white solid. MS m/e: 492.2 [M+H]$^+$.

Example 27 rac-[(3S,4R)-1-(1-Acetyl-piperidine-4-carbonyl)-4-(4-chloro-phenyl)-4-methyl-pyrrolidin-3-yl]-methyl-carbamic acid 4-fluoro-phenyl ester

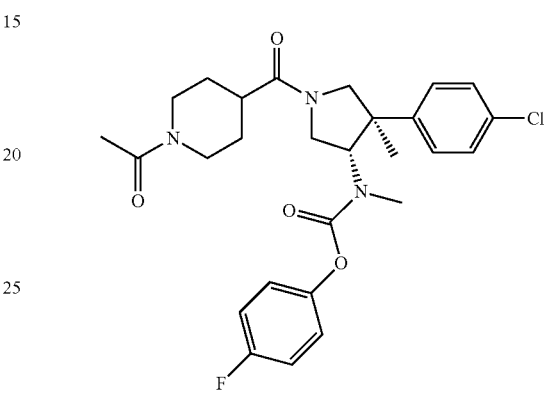

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-acetylpiperidine-4-carboxylic acid as yellow viscous oil. MS m/e: 516.2 [M+H]$^+$.

Example 28 rac-[(3S,4R)-4-(4-Chloro-phenyl)-4-methyl-1-(tetrahydro-pyran-4-carbonyl)-pyrrolidin-3-yl]-methyl-carbamic acid 4-fluoro-phenyl ester

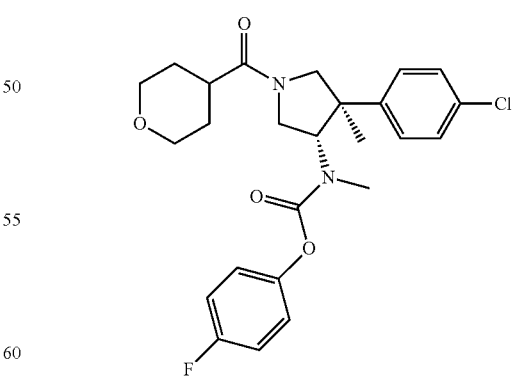

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chlorophenyl)-4-methyl-pyrrolidin-3-yl]-methyl-carbamic acid 4-fluoro-phenyl ester and tetrahydro-2H-pyran-4-carboxylic acid as off-white solid. MS m/e: 475.2 [M+H]⁺.

Example 29 rac-[(3S,4R)-4-(4-Chloro-phenyl)-4-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester

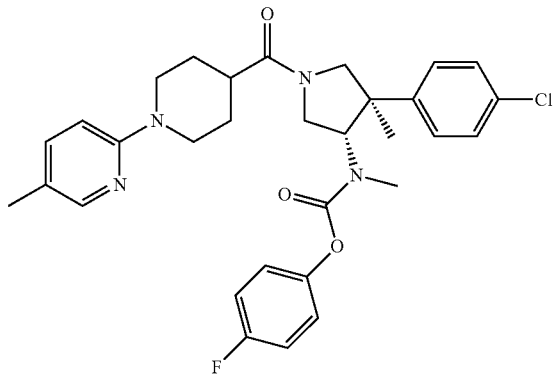 [SMILES: Cc1ccc(N2CCC(C(=O)N3C[C@@H](N(C)C(=O)Oc4ccc(F)cc4)[C@](C)(c4ccc(Cl)cc4)C3)CC2)nc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(5-methylpyridin-2-yl)piperidine-4-carboxylic acid as off-white solid. MS m/e: 565.5 [M+H]⁺.

Example 30 rac-[(3S,4R)-4-(4-Chloro-phenyl)-1-(5'-cyano-3,4,5,6-tetrahydro-2H-[1,2']bipyridinyl-4-carbonyl)-4-methyl-pyrrolidin-3-yl]-methyl-carbamic acid 4-fluoro-phenyl ester

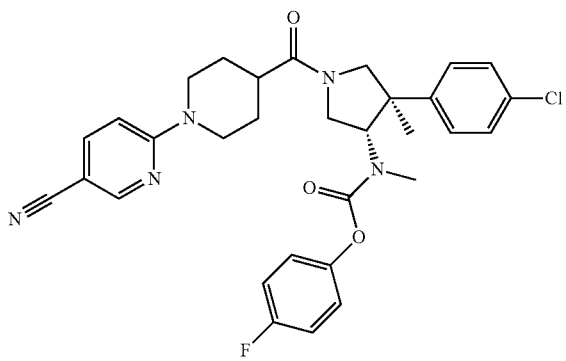 [SMILES: CN(C(=O)Oc1ccc(F)cc1)[C@@H]1CN(C(=O)C2CCN(c3ccc(C#N)cn3)CC2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chlorophenyl)-4-methyl-pyrrolidin-3-yl]-methyl-carbamic acid 4-fluoro-phenyl ester and 1-(5-cyanopyridin-2-yl)piperidine-4-carboxylic acid as yellow viscous oil. MS m/e: 576.3 [M+H]⁺.

Example 31 rac-[(3S,4R)-1-(5'-Acetyl-3,4,5,6-tetrahydro-2H-[1,2']bipyridinyl-4-carbonyl)-4-(4-chloro-phenyl)-4-methyl-pyrrolidin-3-yl]-methyl-carbamic acid 4-fluoro-phenyl ester

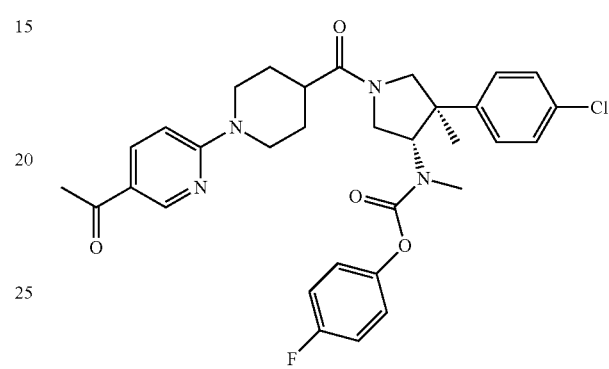

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(5-acetylpyridin-2-yl)piperidine-4-carboxylic acid as off-white solid. MS m/e: 593.4 [M+H]⁺.

Example 32 rac-[(3S,4R)-4-(4-Chloro-phenyl)-1-(5'-chloro-3,4,5,6-tetrahydro-2H-[1,2']bipyridinyl-4-carbonyl)-4-methyl-pyrrolidin-3-yl]-methyl-carbamic acid 4-fluoro-phenyl ester

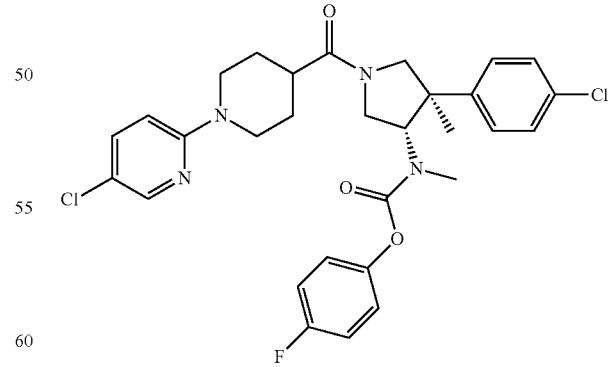

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chlorophenyl)-4-methyl-pyrrolidin-3-yl]-methyl-carbamic acid 4-fluoro-phenyl ester and 1-(5-chloropyridin-2-yl)piperidine-4-carboxylic acid as yellow viscous oil. MS m/e: 585.3 [M+H]+.

Example 33 rac-[(3S,4R)-4-(4-Chloro-phenyl)-4-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester

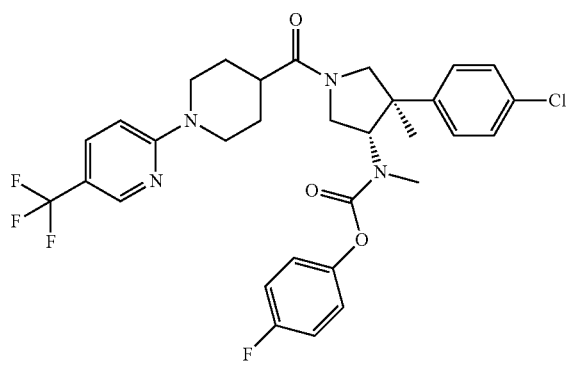 [SMILES: CN(C(=O)Oc1ccc(F)cc1)[C@@H]1CN(C(=O)C2CCN(c3ccc(C(F)(F)F)cn3)CC2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(5-(trifluoromethyl)pyridin-2-yl)piperidine-4-carboxylic acid as yellow viscous oil. MS m/e: 619.5 [M+H]+.

Example 34 rac-[(3S,4R)-4-(4-Chloro-phenyl)-1-(6'-cyano-3,4,5,6-tetrahydro-2H-[1,3']bipyridinyl-4-carbonyl)-4-methyl-pyrrolidin-3-yl]-methyl-carbamic acid 4-fluoro-phenyl ester

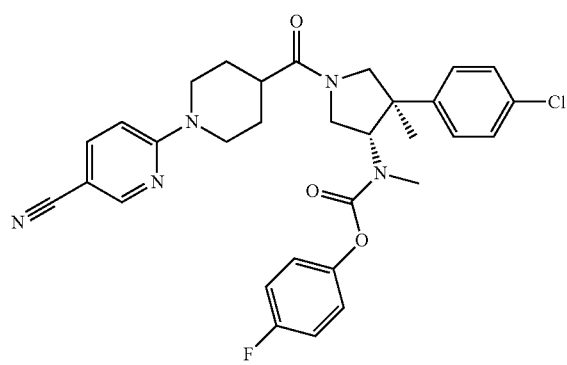 [SMILES: CN(C(=O)Oc1ccc(F)cc1)[C@@H]1CN(C(=O)C2CCN(c3ccc(C#N)cn3)CC2)C[C@@]1(C)c1ccc(Cl)cc1]

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(6-cyanopyridin-3-yl)piperidine-4-carboxylic acid as off-white solid. MS m/e: 576.4 [M+H]+.

Example 35 rac-{(3S,4R)-4-(4-Chloro-phenyl)-1-[1-(6-methoxy-pyridazin-3-yl)-piperidine-4-carbonyl]-4-methyl-pyrrolidin-3-yl}-methyl-carbamic acid 4-fluoro-phenyl ester

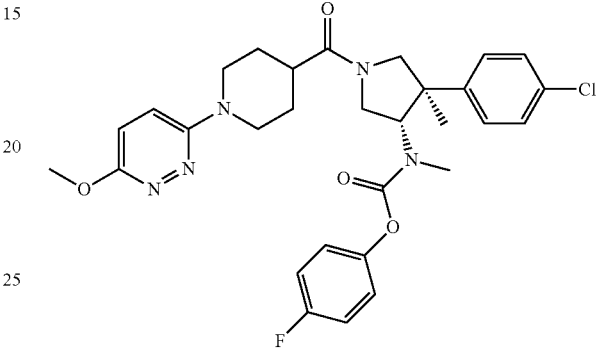

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-phenyl)-4-methyl-pyrrolidin-3-yl]-methyl-carbamic acid 4-fluoro-phenyl ester and 1-(6-methoxypyridazin-3-yl)piperidine-4-carboxylic acid as off-white solid. MS m/e: 582.3 [M+H]+.

Example 36 rac-{(3S,4R)-4-(4-Chloro-phenyl)-4-methyl-1-[4-(2-oxo-piperidin-1-yl)-benzoyl]-pyrrolidin-3-yl}-methyl-carbamic acid 4-fluoro-phenyl ester

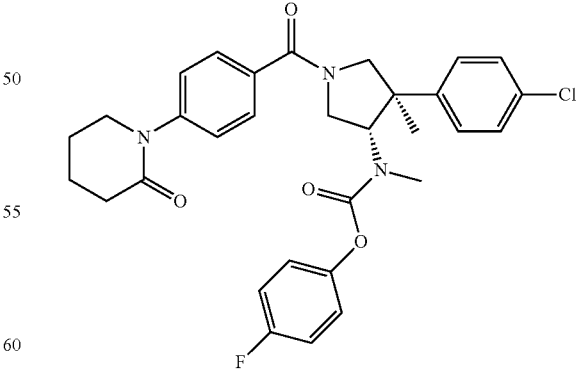

In analogy to the procedure described for the synthesis of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester (example 1, step f) the title compound was prepared from rac-[(3S,4R)-4-(4-Chloro-

The invention claimed is:
1. A compound of formula I

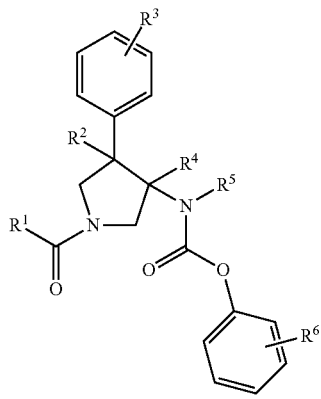

wherein
R¹ is

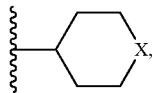

or is phenyl, pyridinyl or pyridazinyl, wherein phenyl, pyridinyl and pyridazinyl are each optionally substituted by cyano, lower alkyl, halogen-substituted phenyl, lower alkyl-substituted [1,2,4]oxadiazol-3-yl or by 2-oxo-piperidin-1-yl;

X is NR or O;
R is —C(O)-lower alkyl, —C(O)-cycloalkyl substituted by lower alkyl, cycloalkyl or is phenyl, pyridinyl or pyridazinyl, wherein phenyl, pyridinyl and pyridazinyl are each optionally substituted by lower alkyl, lower alkoxy, cyano, —C(O)-lower alkyl, halogen or lower alkyl substituted by halogen;
R² is hydrogen or lower alkyl;
R³ is hydrogen, halogen, cyano, lower alkyl or lower alkyl substituted by halogen;
R⁴ is hydrogen or lower alkyl; wherein R² and R⁴ are not simultaneously hydrogen or lower alkyl;
R⁵ is lower alkyl; and
R⁶ is halogen, hydroxy, lower alkyl, lower alkoxy, lower alkyl substituted by halogen, S(O)₂-lower alkyl or cyano;
or a pharmaceutically active salt, sterioisomer or racemic or non-racemic mixture thereof.

2. The compound of claim 1, wherein R⁴ is methyl and R² is hydrogen.

3. The compound of claim 2, selected from the group consisting of
rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester;
rac-[(3R,4S)-4-(4-Chloro-phenyl)-1-(1-cyclohexyl-piperidine-4-carbonyl)-3-methyl-pyrrolidin-3-yl]-methyl-carbamic acid 4-fluoro-phenyl ester;
rac-[(3R,4S)-4-(4-Chloro-phenyl)-1-(4-cyano-benzoyl)-3-methyl-pyrrolidin-3-yl]-methyl-carbamic acid 4-fluoro-phenyl ester;
rac-[(3R,4S)-1-(1-Acetyl-piperidine-4-carbonyl)-4-(4-chloro-phenyl)-3-methyl-pyrrolidin-3-yl]-methyl-carbamic acid 4-fluoro-phenyl ester;
rac-[(3R,4S)-4-(4-Chloro-phenyl)-3-methyl-1-(tetrahydro-pyran-4-carbonyl)-pyrrolidin-3-yl]-methyl-carbamic acid 4-fluoro-phenyl ester;
rac-[(3R,4S)-4-(4-Chloro-phenyl)-3-methyl-1-(6-methyl-pyridazine-4-carbonyl)-pyrrolidin-3-yl]-methyl-carbamic acid 4-fluoro-phenyl ester;
rac-{(3R,4S)-4-(4-Chloro-phenyl)-3-methyl-1-[1-(1-methyl-cyclopropanecarbonyl)-piperidine-4-carbonyl]-pyrrolidin-3-yl}-methyl-carbamic acid 4-fluoro-phenyl ester;
rac-[(3R,4S)-4-(4-Chloro-phenyl)-3-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;
rac-[(3R,4S)-4-(4-Chloro-phenyl)-1-(5'-cyano-3,4,5,6-tetrahydro-2H-[1,2']bipyridinyl-4-carbonyl)-3-methyl-pyrrolidin-3-yl]-methyl-carbamic acid 4-fluoro-phenyl ester; and
rac-{(3R,4S)-4-(4-Chloro-phenyl)-1-[1-(4-cyano-phenyl)-piperidine-4-carbonyl]-3-methyl-pyrrolidin-3-yl}-methyl-carbamic acid 4-fluoro-phenyl ester.

4. The compound of claim 2, selected from the group consisting of
rac-[(3R,4S)-1-(5'-Acetyl-3,4,5,6-tetrahydro-2H-[1,2']bipyridinyl-4-carbonyl)-4-(4-chloro-phenyl)-3-methyl-pyrrolidin-3-yl]-methyl-carbamic acid 4-fluoro-phenyl ester;
rac-[(3R,4S)-4-(4-Chloro-phenyl)-1-(5'-fluoro-3,4,5,6-tetrahydro-2H-[1,2']bipyridinyl-4-carbonyl)-3-methyl-pyrrolidin-3-yl]-methyl-carbamic acid 4-fluoro-phenyl ester;
rac-[(3R,4S)-4-(4-Chloro-phenyl)-1-(5'-chloro-3,4,5,6-tetrahydro-2H-[1,2']bipyridinyl-4-carbonyl)-3-methyl-pyrrolidin-3-yl]-methyl-carbamic acid 4-fluoro-phenyl ester;
rac-[(3R,4S)-4-(4-Chloro-phenyl)-1-(6-cyano-pyridine-3-carbonyl)-3-methyl-pyrrolidin-3-yl]-methyl-carbamic acid 4-fluoro-phenyl ester;
rac-[(3R,4S)-4-(4-Chloro-phenyl)-3-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;
rac-[(3R,4S)-4-(4-Chloro-phenyl)-1-(4'-fluoro-biphenyl-4-carbonyl)-3-methyl-pyrrolidin-3-yl]-methyl-carbamic acid 4-fluoro-phenyl ester;
rac-{(3R,4S)-4-(4-Chloro-phenyl)-3-methyl-1-[4-(5-methyl-[1,2,4]oxadiazol-3-yl)-benzoyl]-pyrrolidin-3-yl}-methyl-carbamic acid 4-fluoro-phenyl ester;
rac-[(3R,4S)-4-(4-Chloro-phenyl)-1-(6'-cyano-3,4,5,6-tetrahydro-2H-[1,3']bipyridinyl-4-carbonyl)-3-methyl-pyrrolidin-3-yl]-methyl-carbamic acid 4-fluoro-phenyl ester;
rac-{(3R,4S)-4-(4-Chloro-phenyl)-1-[1-(6-methoxy-pyridazin-3-yl)-piperidine-4-carbonyl]-3-methyl-pyrrolidin-3-yl}-methyl-carbamic acid 4-fluoro-phenyl ester; and
rac-{(3R,4S)-4-(4-Chloro-phenyl)-3-methyl-1-[4-(2-oxopiperidin-1-yl)-benzoyl]-pyrrolidin-3-yl}-methyl-carbamic acid 4-fluoro-phenyl ester.

5. A compound of claim 1, wherein R⁴ is hydrogen and R² is methyl.

6. A compound of claim 5, selected from the group consisting of rac-{(3S,4R)-4-(4-Chloro-phenyl)-4-methyl-1-[1-(1-methyl-cyclopropanecarbonyl)-piperidine-4-carbonyl]-pyrrolidin-3-yl}-methyl-carbamic acid 4-fluoro-phenyl ester;

rac-{(3S,4R)-4-(4-Chloro-phenyl)-1-[1-(4-cyano-phenyl)-piperidine-4-carbonyl]-4-methyl-pyrrolidin-3-yl}-methyl-carbamic acid 4-fluoro-phenyl ester;

rac-[(3S,4R)-4-(4-Chloro-phenyl)-1-(5'-fluoro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-1-(1-isobutyryl-piperidine-4-carbonyl)-4-methyl-pyrrolidin-3-yl]-methyl-carbamic acid 4-fluoro-phenyl ester;

[(3S,4R)-4-(4-Chloro-phenyl)-1-(1-cyclohexyl-piperidine-4-carbonyl)-4-methyl-pyrrolidin-3-yl]-methyl-carbamic acid 4-fluoro-phenyl ester;

rac-[(3S,4R)-4-(4-Chloro-phenyl)-1-(4-cyano-benzoyl)-4-methyl-pyrrolidin-3-yl]-methyl-carbamic acid 4-fluoro-phenyl ester;

rac-[(3S,4R)-1-(1-Acetyl-piperidine-4-carbonyl)-4-(4-chloro-phenyl)-4-methyl-pyrrolidin-3-yl]-methyl-carbamic acid 4-fluoro-phenyl ester; and rac-[(3S,4R)-4-(4-Chloro-phenyl)-4-methyl-1-(tetrahydro-pyran-4-carbonyl)-pyrrolidin-3-yl]-methyl-carbamic acid 4-fluoro-phenyl ester.

7. A compound of claim 5, selected from the group consisting of rac-[(3S,4R)-4-(4-Chloro-phenyl)-4-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(5'-cyano-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-1-(5'-Acetyl-3,4,5,6-tetrahydro-2H-[1,2']bipyridinyl-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-1-(5'-chloro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-4-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(6'-cyano-3,4,5,6-tetrahydro-2H-[1,3']bipyridinyl-4-carbonyl)-4-methyl-pyrrolidin-3-yl]-methyl-carbamic acid 4-fluoro-phenyl ester;

rac-{(3S,4R)-4-(4-Chloro-phenyl)-1-[1-(6-methoxy-pyridazin-3-yl)-piperidine-4-carbonyl]-4-methyl-pyrrolidin-3-yl}-methyl-carbamic acid 4-fluoro-phenyl ester; and rac-{(3S,4R)-4-(4-Chloro-phenyl)-4-methyl-1-[4-(2-oxo-piperidin-1-yl)-benzoyl]-pyrrolidin-3-yl}-methyl-carbamic acid 4-fluoro-phenyl ester.

8. The compound of claim 1, having formula Ia

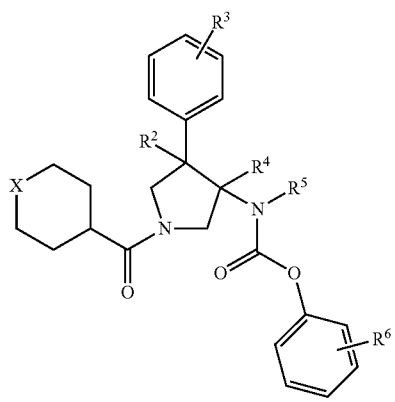

Ia wherein
R$^1$ is

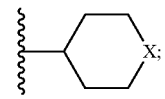

X is NR or O;
R is —C(O)-lower alkyl, —C(O)-cycloalkyl substituted by lower alkyl, cycloalkyl or is phenyl, pyridinyl or pyridazinyl, wherein phenyl, pyridinyl and pyridazinyl are each optionally substituted by lower alkyl, lower alkoxy, cyano, —C(O)-lower alkyl, halogen or lower alkyl substituted by halogen;
R$^2$ is hydrogen or lower alkyl;
R$^3$ is hydrogen, halogen, cyano, lower alkyl or lower alkyl substituted by halogen;
R$^4$ is hydrogen or lower alkyl; wherein R$^2$ and R$^4$ are not simultaneously hydrogen or lower alkyl;
R$^5$ is lower alkyl; and
R$^6$ is halogen, hydroxy, lower alkyl, lower alkoxy, lower alkyl substituted by halogen, S(O)$_2$-lower alkyl or cyano;
or a pharmaceutically active salt, sterioisomer or racemic or non-racemic mixture thereof.

9. The compound of claim 8, wherein X is NR.

10. The compound of claim 9, selected from the group consisting of rac-[(3R,4S)-4-(4-Chloro-phenyl)-1-(1-isobutyryl-piperidine-4-carbonyl)-3-methyl-pyrrolidin-3-yl]-methyl-carbamic acid 4-fluoro-phenyl ester;

rac-[(3R,4S)-4-(4-Chloro-phenyl)-1-(1-cyclohexyl-piperidine-4-carbonyl)-3-methyl-pyrrolidin-3-yl]-methyl-carbamic acid 4-fluoro-phenyl ester;

rac-[(3R,4S)-1-(1-Acetyl-piperidine-4-carbonyl)-4-(4-chloro-phenyl)-3-methyl-pyrrolidin-3-yl]-methyl-carbamic acid 4-fluoro-phenyl ester;

rac-{(3R,4S)-4-(4-Chloro-phenyl)-3-methyl-1-[1-(1-methyl-cyclopropanecarbonyl)-piperidine-4-carbonyl]-pyrrolidin-3-yl}-methyl-carbamic acid 4-fluoro-phenyl ester;

rac-[(3R,4S)-4-(4-Chloro-phenyl)-3-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3R,4S)-4-(4-Chloro-phenyl)-1-(5'-cyano-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-{(3R,4S)-4-(4-Chloro-phenyl)-1-[1-(4-cyano-phenyl)-piperidine-4-carbonyl]-3-methyl-pyrrolidin-3-yl}-methyl-carbamic acid 4-fluoro-phenyl ester;

rac-[(3R,4S)-1-(5'-Acetyl-3,4,5,6-tetrahydro-2H-[1,2']bipyridinyl-4-carbonyl)-4-(4-chloro-phenyl)-3-methyl-pyrrolidin-3-yl]-methyl-carbamic acid 4-fluoro-phenyl ester; and rac-[(3R,4S)-4-(4-Chloro-phenyl)-1-(5'-fluoro-3,4,5,6-tetrahydro-2H-[1,2']bipyridinyl-4-carbonyl)-3-methyl-pyrrolidin-3-yl]-methyl-carbamic acid 4-fluoro-phenyl ester.

11. The compound of claim 9, selected from the group consisting of rac-[(3R,4S)-4-(4-Chloro-phenyl)-1-(5'-chloro-3,4,5,6-tetrahydro-2H-[1,2']bipyridinyl-4-carbonyl)-3-methyl-pyrrolidin-3-yl]-methyl-carbamic acid 4-fluoro-phenyl ester;

rac-[(3R,4S)-4-(4-Chloro-phenyl)-3-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

rac-[(3R,4S)-4-(4-Chloro-phenyl)-1-(6'-cyano-3,4,5,6-tetrahydro-2H-[1,3']bipyridinyl-4-carbonyl)-3-methyl-pyrrolidin-3-yl]-methyl-carbamic acid 4-fluoro-phenyl ester;

rac-{(3R,4S)-4-(4-Chloro-phenyl)-1-[1-(6-methoxy-pyridazin-3-yl)-piperidine-4-carbonyl]-3-methyl-pyrrolidin-3-yl}-methyl-carbamic acid 4-fluoro-phenyl ester;

rac-{(3S,4R)-4-(4-Chloro-phenyl)-4-methyl-1-[1-(1-methyl-cyclopropanecarbonyl)-piperidine-4-carbonyl]-pyrrolidin-3-yl}-methyl-carbamic acid 4-fluoro-phenyl ester;

rac-{(3S,4R)-4-(4-Chloro-phenyl)-1-[1-(4-cyano-phenyl)-piperidine-4-carbonyl]-4-methyl-pyrrolidin-3-yl}-methyl-carbamic acid 4-fluoro-phenyl ester;

rac-[(3S,4R)-4-(4-Chloro-phenyl)-1-(5'-fluoro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-1-(1-isobutyryl-piperidine-4-carbonyl)-4-methyl-pyrrolidin-3-yl]-methyl-carbamic acid 4-fluoro-phenyl ester; and

[(3S,4R)-4-(4-Chloro-phenyl)-1-(1-cyclohexyl-piperidine-4-carbonyl)-4-methyl-pyrrolidin-3-yl]-methyl-carbamic acid 4-fluoro-phenyl ester.

12. The compound of claim 9, selected from the group consisting of rac-[(3S,4R)-1-(1-Acetyl-piperidine-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-4-methyl-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(5'-cyano-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-1-(5'-Acetyl-3,4,5,6-tetrahydro-2H-[1,2']bipyridinyl-4-carbonyl)-4-(4-chloro-phenyl)-4-methyl-pyrrolidin-3-yl]-methyl-carbamic acid 4-fluoro-phenyl ester;

rac-[(3S,4R)-4-(4-Chloro-phenyl)-1-(5'-chloro-3,4,5,6-tetrahydro-2H-[1,2']bipyridinyl-4-carbonyl)-4-methyl-pyrrolidin-3-yl]-methyl-carbamic acid 4-fluoro-phenyl ester;

rac-[(3S,4R)-4-(4-Chloro-phenyl)-4-methyl-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

rac-[(3S,4R)-4-(4-Chloro-phenyl)-1-(6'-cyano-3,4,5,6-tetrahydro-2H-[1,3']bipyridinyl-4-carbonyl)-4-methyl-pyrrolidin-3-yl]-methyl-carbamic acid 4-fluoro-phenyl ester and rac-{(3S,4R)-4-(4-Chloro-phenyl)-1-[1-(6-methoxy-pyridazin-3-yl)-piperidine-4-carbonyl]-4-methyl-pyrrolidin-3-yl}-methyl-carbamic acid 4-fluoro-phenyl ester.

13. The compound of claim 8, wherein X is O.

14. The compound of claim 13, selected from the group consisting of rac-[(3R,4S)-4-(4-Chloro-phenyl)-3-methyl-1-(tetrahydro-pyran-4-carbonyl)-pyrrolidin-3-yl]-methyl-carbamic acid 4-fluoro-phenyl ester and rac-[(3S,4R)-4-(4-Chloro-phenyl)-4-methyl-1-(tetrahydro-pyran-4-carbonyl)-pyrrolidin-3-yl]-methyl-carbamic acid 4-fluoro-phenyl ester.

15. The compound of claim 1, having formula Ib

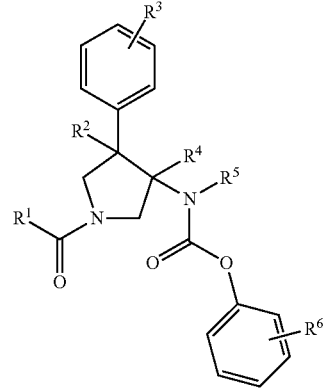

wherein

R$^1$ is phenyl, pyridinyl or pyridazinyl, wherein phenyl, pyridinyl and pyridazinyl are each optionally substituted by cyano, lower alkyl, halogen-substituted phenyl, lower alkyl-substituted [1,2,4]oxadiazol-3-yl or by 2-oxo-piperidin-1-yl;

R$^2$ is hydrogen or lower alkyl;

R$^3$ is hydrogen, halogen, cyano, lower alkyl or lower alkyl substituted by halogen;

R$^4$ is hydrogen or lower alkyl; wherein R$^2$ and R$^4$ are not simultaneously hydrogen or lower alkyl;

R$^5$ is lower alkyl; and

R$^6$ is halogen, hydroxy, lower alkyl, lower alkoxy, lower alkyl substituted by halogen, S(O)$_2$-lower alkyl or cyano;

or a pharmaceutically active salt, sterioisomer or racemic or non-racemic mixture thereof.

16. The compound of claim 15, selected from the group consisting of rac-[(3R,4S)-4-(4-Chloro-phenyl)-1-(4-cyano-benzoyl)-3-methyl-pyrrolidin-3-yl]-methyl-carbamic acid 4-fluoro-phenyl ester;

rac-[(3R,4S)-4-(4-Chloro-phenyl)-3-methyl-1-(6-methyl-pyridazine-4-carbonyl)-pyrrolidin-3-yl]-methyl-carbamic acid 4-fluoro-phenyl ester;

rac-[(3R,4S)-4-(4-Chloro-phenyl)-1-(6-cyano-pyridine-3-carbonyl)-3-methyl-pyrrolidin-3-yl]-methyl-carbamic acid 4-fluoro-phenyl ester;

rac-[(3R,4S)-4-(4-Chloro-phenyl)-1-(4'-fluoro-biphenyl-4-carbonyl)-3-methyl-pyrrolidin-3-yl]-methyl-carbamic acid 4-fluoro-phenyl ester;

rac-{(3R,4S)-4-(4-Chloro-phenyl)-3-methyl-1-[4-(5-methyl-[1,2,4]oxadiazol-3-yl)-benzoyl]-pyrrolidin-3-yl}-methyl-carbamic acid 4-fluoro-phenyl ester;

rac-{(3R,4 S)-4-(4-Chloro-phenyl)-3-methyl-1-[4-(2-oxo-piperidin-1-yl)-benzoyl]-pyrrolidin-3-yl}-methyl-carbamic acid 4-fluoro-phenyl ester;

rac-[(3S,4R)-4-(4-Chloro-phenyl)-1-(4-cyano-benzoyl)-4-methyl-pyrrolidin-3-yl]-methyl-carbamic acid 4-fluoro-phenyl ester and rac-{(3S,4R)-4-(4-Chloro-phenyl)-4-methyl-1-[4-(2-oxo-piperidin-1-yl)-benzoyl]-pyrrolidin-3-yl}-methyl-carbamic acid 4-fluoro-phenyl ester.

17. A pharmaceutical composition comprising a therapeutically effective amount of a compound of formula I

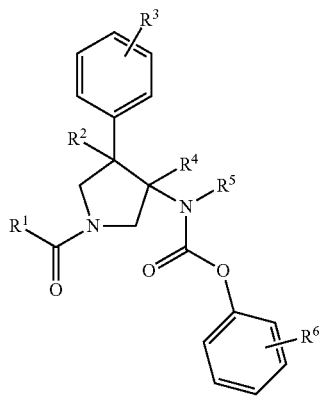

wherein $R^1$ is

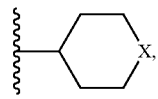

or is phenyl, pyridinyl or pyridazinyl, wherein phenyl, pyridinyl and pyridazinyl are each optionally substituted by cyano, lower alkyl, halogen-substituted phenyl, lower alkyl-substituted [1,2,4]oxadiazol-3-yl or by 2-oxo-piperidin-1-yl;

X is NR or O;

R is —C(O)-lower alkyl, —C(O)-cycloalkyl substituted by lower alkyl, cycloalkyl or is phenyl, pyridinyl or pyridazinyl, wherein phenyl, pyridinyl and pyridazinyl are each optionally substituted by lower alkyl, lower alkoxy, cyano, —C(O)-lower alkyl, halogen or lower alkyl substituted by halogen;

$R^2$ is hydrogen or lower alkyl;

$R^3$ is hydrogen, halogen, cyano, lower alkyl or lower alkyl substituted by halogen;

$R^4$ is hydrogen or lower alkyl; wherein $R^2$ and $R^4$ are not simultaneously hydrogen or lower alkyl;

$R^5$ is lower alkyl; and $R^6$ is halogen, hydroxy, lower alkyl, lower alkoxy, lower alkyl substituted by halogen, $S(O)_2$-lower alkyl or cyano;

or a pharmaceutically active salt, sterioisomer or racemic or non-racemic mixture thereof and a pharmaceutically acceptable carrier.

* * * * *